United States Patent
Champion et al.

(10) Patent No.: US 10,695,359 B2
(45) Date of Patent: Jun. 30, 2020

(54) TERNARY MIXTURES OF 6'-SL, LNNT AND LST C

(71) Applicant: Glycom A/S, Hørsholm (DK)

(72) Inventors: Elise Champion, Toulouse (FR); Bruce McConnell, La Tour de Peilz (CH); Gyula Dekany, Sinnamon Park (AU)

(73) Assignee: GLYCOM A/S, Hørsholm (DK)

( * ) Notice: Subject to any disclaimer, the term of this patent is extended or adjusted under 35 U.S.C. 154(b) by 0 days.

(21) Appl. No.: 15/579,818

(22) PCT Filed: Jun. 9, 2016

(86) PCT No.: PCT/IB2016/053412
§ 371 (c)(1),
(2) Date: Dec. 5, 2017

(87) PCT Pub. No.: WO2016/199071
PCT Pub. Date: Dec. 15, 2016

(65) Prior Publication Data
US 2018/0161350 A1    Jun. 14, 2018

(30) Foreign Application Priority Data
Jun. 9, 2015 (EP) ................................. 15171177

(51) Int. Cl.
| | | |
|---|---|---|
| A61K 31/702 | (2006.01) | |
| C07H 3/04 | (2006.01) | |
| C07H 5/06 | (2006.01) | |
| C07H 1/00 | (2006.01) | |
| A61P 31/12 | (2006.01) | |
| A61P 31/04 | (2006.01) | |
| C07H 3/06 | (2006.01) | |
| C12P 19/18 | (2006.01) | |

(52) U.S. Cl.
CPC ............ *A61K 31/702* (2013.01); *A61P 31/04* (2018.01); *A61P 31/12* (2018.01); *C07H 1/00* (2013.01); *C07H 3/04* (2013.01); *C07H 3/06* (2013.01); *C07H 5/06* (2013.01); *C12P 19/18* (2013.01); *C12Y 204/99* (2013.01)

(58) Field of Classification Search
CPC .... A61K 31/7016; A61K 31/702; C07H 1/00; C07H 3/04; C07H 3/06; C07H 5/06; A61P 31/04; A61P 31/12; C12P 19/18; C12Y 204/99; C12Y 204/99001; C12Y 204/99003; C12N 9/1048; C12N 9/1051
See application file for complete search history.

(56) References Cited

U.S. PATENT DOCUMENTS

| | | | |
|---|---|---|---|
| 5,827,714 A | 10/1998 | Yamamoto et al. | |
| 6,255,094 B1 | 7/2001 | Yamamoto et al. | |
| 7,993,875 B2 | 8/2011 | Tsukamoto et al. | |
| 8,187,838 B2 | 5/2012 | Tsukamoto et al. | |
| 8,187,853 B2 | 5/2012 | Yamamoto et al. | |
| 8,372,617 B2 | 2/2013 | Yamamoto et al. | |
| 2012/0184016 A1 | 7/2012 | Mine et al. | |

FOREIGN PATENT DOCUMENTS

| | | | |
|---|---|---|---|
| AU | 780290 B2 | 3/2005 | |
| EP | 0577580 A2 | 1/1994 | |
| EP | 1332759 A1 | 8/2003 | |
| WO | 2007101862 A1 | 9/2007 | |
| WO | 2010115934 A1 | 10/2010 | |
| WO | 2011100979 A1 | 8/2011 | |
| WO | 2011100980 A1 | 8/2011 | |
| WO | 2012155916 A1 | 11/2012 | |
| WO | 2012156897 A1 | 11/2012 | |
| WO | 2012156898 A1 | 11/2012 | |
| WO | WO-2012156273 A1 * | 11/2012 | ............... C07H 5/06 |
| WO | 2013044928 A1 | 4/2013 | |
| WO | 2013091660 A1 | 6/2013 | |
| WO | 2013139344 A1 | 9/2013 | |
| WO | 2013148134 A1 | 10/2013 | |
| WO | 2013185780 A1 | 12/2013 | |

OTHER PUBLICATIONS

Thurl, S. et al "Variation of human milk oligosaccharides . . . " Br. J. Nutr., vol. 104, pp. 1261-1271. (Year: 2010).*
Klindworth, A., et al. "Evaluation of general 16S ribosomal RNA gene PCR primers for classical and next-generation sequencing-based diversity studies," Nucleic Acids Research, 2013, vol. 41(1), pp. 1-11.
Mine, T. et al., "An alpha2,6-sialyltransferase cloned from *Photobacterium leiognathi* strain JT-SHIZ-119 shows both sialyltransferase and neuraminidase activity," Glycobiology, 2010, vol. 20(2), pp. 158-165.
Tsukamoto, H. et al., "*Photobacterium* sp. JT-ISH-224 Produces Two Sialyltransferases, alpha-/beta-Galactoside alpha2,3-Sialyltransferase and beta-Galactoside alpha2,6-Sialyltransferase," J. Biochem., 2008, vol. 143, pp. 187-197.
Urashima, T. et al. (2011) Nutrition and Diet Research Progress: Milk Oligosaccharides. New York: Nova Science Publishers, Inc.
Yamamoto, T. et al., "Cloning and Expression of a Marine Bacterial beta-Galactoside alpha2,6-Sialyltransferase Gene from *Photobacterium damsela* JT0160," J. Biochem., 1998, vol. 123, pp. 94-100.
Yamamoto, T. et al., A beta-galactoside alpha2,6-sialyltransferase produced by a marine bacterium, *Photobacterium leiognathi* JT-SHIZ-145, is active at pH 8, Glycobiology, 2007, vol. 17, pp. 1167-1174.

* cited by examiner

*Primary Examiner* — Leigh C Maier

(74) *Attorney, Agent, or Firm* — Neal, Gerber & Eisenberg LLP

(57) ABSTRACT

A mixture of human milk oligosaccharides that consists essentially of 6'-SL, LNnT and LSTc, made by treating 6'-SL and LNnT in the presence of an α2,6-transsialidase.

20 Claims, 3 Drawing Sheets

Specification includes a Sequence Listing.

```
SEQ ID NO. 1    MCNDNQNTVDVVVSTVNDNVIENNTYQVKPIDTPTTFDSYSWIQTCGTPILKDDEKYSLS  60
SEQ ID NO. 2    MCNDNQNTVDVVVSTVNDNVIENNTYQVKPIDTPTTFDSYSWIQTCGTPILKDDEKYSLS  60
SEQ ID NO. 3    MCNSDNTSLKETVSSNSADVVETETYQLTPIDAPSSFLSHSWEQTCGTPILNESDKQAIS  60

SEQ ID NO. 1    FDFVAPELDQDEKFCFEFTGDVDGKRYVTQTNLTVVAPTLEVYVDHASLPSLQQLMKIIQ  120
SEQ ID NO. 2    FDFVAPELDQDEKFCFEFTGDVDGKRYVTQTNLTVVAPTLEVYVDHASLPSLQQLMKIIQ  120
SEQ ID NO. 3    FDFVAPELKQDEKYCFTFKGITGDHRYITNTTLTVVAPTLEVYIDHASLPSLQQLIHIIQ  120

SEQ ID NO. 1    QKNEYSQNERFISWGRIGLTEDNAEKLNAHIYPLAGNNTSQELVDAVIDYADSKNRLNLE  180
SEQ ID NO. 2    QKNEYSQNERFISWGRIRLTEDNAEKLNAHIYPLAGNNTSQELVDAVIDYADSKNRLNLE  180
SEQ ID NO. 3    AKDEYPSNQRFVSWKRVTVDADNANKLNIHTYPLKGNNTSPEMVAAIDEYAQSKNRLNIE  180

SEQ ID NO. 1    LNTNTAHSFPNLAPILRIISSKSNILISNINLYDDGSAEYVNLYNWKDTEDKSVKLSDSF  240
SEQ ID NO. 2    LNTNTGHSFRNIAPILRATSSKNNILISNINLYDDGSAEYVSLYNWKDTDNKSQKLSDSF  240
SEQ ID NO. 3    FYTNTAHVFNNLPPIIQPLYNNEKVKISHISLYDDGSSEYVSLYQWKDTPNKIETLEGEV  240

SEQ ID NO. 1    LVLKDYFNGISSEKPSGIYGRYNWHQLYNTSYYFLRKDYLTVEPQLHDLREYLGGSLKQM  300
SEQ ID NO. 2    LVLKDYLNGISSEKPNGIYSIYNWHQLYHSSYYFLRKDYLTVETKLHDLREYLGGSLKQM  300
SEQ ID NO. 3    SLLANYLAGTSPDAPKGMGNRYNWHKLYDTDYYFLREDYLDVEANLHDLRDYLGSSAKQM  300

SEQ ID NO. 1    SWDGFSQLSKGDKELFLNIVGFDQEKLQQEYQQSELPNFVFTGTTTWAGGETKEYYAQQQ  360
SEQ ID NO. 2    SWDTFSQLSKGDKELFLNIVGFDQEKLQQEYQQSELPNFVFTGTTTWAGGETKEYYAQQQ  360
SEQ ID NO. 3    PWDEFAKLSDSQQTLFLDIVGFDKEQLQQQYSQSPLPNFIFTGTTTWAGGETKEYYAQQQ  360

SEQ ID NO. 1    VNVVNNAINETSPYYLGREHDLFFKGHPRGGIINDIILGSFNNMIDIPAKVSFEVLMMTG  420
SEQ ID NO. 2    VNVVNNAINETSPYYLGREHDLFFKGHPRGGIINDIILGSFNNMIDIPAKVSFEVLMMTG  420
SEQ ID NO. 3    VNVINNAINETSPYYLGKDYDLFFKGHPAGGVINDIILGSFPDMINIPAKISFEVLMMTD  420

SEQ ID NO. 1    MLPDTVGGIASSLYFSIPAEKVSFIVFTSSDTITDREDALKSPLVQVMMTLGIVKEKDVL  480
SEQ ID NO. 2    MLPDTVGGIASSLYFSIPAEKVSFIVFTSSDTITDREDALKSPLVQVMMTLGIVKEKDVL  480
SEQ ID NO. 3    MLPDTVAGIASSLYFTIPADKVNFIVFTSSDTITDREEALKSPLVQVMLTLGIVKEKDVL  480

SEQ ID NO. 1    FWSDLPDCSSGVCIAQY--------------------------------------------  497
SEQ ID NO. 2    FWC----------------------------------------------------------  483
SEQ ID NO. 3    FWADHKVNSMEVAIDEACTRIIAKRQPTASDLRLVIAIIKTITDLERIGDVAESIAKVAL  540

SEQ ID NO. 1    ------------------------------------------------------------  497
SEQ ID NO. 2    ------------------------------------------------------------  483
SEQ ID NO. 3    ESFSNKQYNLLVSLESLGQHTVRMLHEVLDAFARMDVKAAIEVYQEDDRIDQEYESIVRQ  600

SEQ ID NO. 1    ------------------------------------------------------------  497
SEQ ID NO. 2    ------------------------------------------------------------  483
SEQ ID NO. 3    LMAHMMEDPSSIPNVMKVMWAARSIERVGDRCQNICEYIIYFVKGKDVRHTKPDDFGTML  660

SEQ ID NO. 1    - 497
SEQ ID NO. 2    - 483
SEQ ID NO. 3    D 661
```

Figure 1

```
SEQ ID NO. 1      1 MCNDNQNTVDVVVSTVNDNVIENNTYQVKPIDTPTTFDSYSWIQTCGTPI    50
                    ||||||||||||||||||||||||||||||||||||||||||||||||||
SEQ ID NO. 2      1 MCNDNQNTVDVVVSTVNDNVIENNTYQVKPIDTPTTFDSYSWIQTCGTPI    50

SEQ ID NO. 1     51 LKDDEKYSLSFDFVAPELDQDEKFCFEFTGDVDGKRYVTQTNLTVVAPTL   100
                    ||||||||||||||||||||||||||||||||||||||||||||||||||
SEQ ID NO. 2     51 LKDDEKYSLSFDFVAPELDQDEKFCFEFTGDVDGKRYVTQTNLTVVAPTL   100

SEQ ID NO. 1    101 EVYVDHASLPSLQQLMKIIQQKNEYSQNERFISWGRIGLTEDNAEKLNAH   150
                    |||||||||||||||||||||||||||||||||||||||.||||||||||
SEQ ID NO. 2    101 EVYVDHASLPSLQQLMKIIQQKNEYSQNERFISWGRIRLTEDNAEKLNAH   150

SEQ ID NO. 1    151 IYPLAGNNTSQELVDAVIDYADSKNRLNLELNTNTAHSFPNLAPILRIIS   200
                    |||||||||||||||||||||||||||||||||.|||.|:|||||||..|
SEQ ID NO. 2    151 IYPLAGNNTSQELVDAVIDYADSKNRLNLELNTNTGHSFRNIAPILRATS   200

SEQ ID NO. 1    201 SKSNILISNINLYDDGSAEYVNLYNWKDTEDKSVKLSDSFLVLKDYFNGI   250
                    ||:|||||||||||||||||:|||||||:||.||||||||||||||.|||
SEQ ID NO. 2    201 SKNNILISNINLYDDGSAEYVSLYNWKDTDNKSQKLSDSFLVLKDYLNGI   250

SEQ ID NO. 1    251 SSEKPSGIYGRYNWHQLYNTSYYFLRKDYLTVEPQLHDLREYLGGSLKQM   300
                    |||||:|||..||||||::|||||||||||||.:||||||||||||||||
SEQ ID NO. 2    251 SSEKPNGIYSIYNWHQLYHSSYYFLRKDYLTVETKLHDLREYLGGSLKQM   300

SEQ ID NO. 1    301 SWDGFSQLSKGDKELFLNIVGFDQEKLQQEYQQSELPNFVFTGTTTWAGG   350
                    |||.||||||||||||||||||||||||||||||||||||||||||||||
SEQ ID NO. 2    301 SWDTFSQLSKGDKELFLNIVGFDQEKLQQEYQQSELPNFVFTGTTTWAGG   350

SEQ ID NO. 1    351 ETKEYYAQQQVNVVNNAINETSPYYLGREHDLFFKGHPRGGIINDIILGS   400
                    ||||||||||||||||||||||||||||||||||||||||||||||||||
SEQ ID NO. 2    351 ETKEYYAQQQVNVVNNAINETSPYYLGREHDLFFKGHPRGGIINDIILGS   400

SEQ ID NO. 1    401 FNNMIDIPAKVSFEVLMMTGMLPDTVGGIASSLYFSIPAEKVSFIVFTSS   450
                    ||||||||||||||||||||||||||||||||||||||||||||||||||
SEQ ID NO. 2    401 FNNMIDIPAKVSFEVLMMTGMLPDTVGGIASSLYFSIPAEKVSFIVFTSS   450

SEQ ID NO. 1    451 DTITDREDALKSPLVQVMMTLGIVKEKDVLFWSDLPDCSSGVCIAQY      497
                    |||||||||||||||||||||||||||||||.
SEQ ID NO. 2    451 DTITDREDALKSPLVQVMMTLGIVKEKDVLFWC---------------    483
```

Figure 2.

```
SEQ ID NO. 1    1 MCNDNQNTVDVVVSTVNDNVIENNTYQVKPIDTPTTFDSYSWIQTCGTPI   50
                  |||.:..::...||:.:.:||:|..|||:.|||.|::|.:||.|||||||
SEQ ID NO. 3    1 MCNSDNTSLKETVSSNSADVVETETYQLTPIDAPSSFLSHSWEQTCGTPI   50

SEQ ID NO. 1   51 LKDDEKYSLSFDFVAPELDQDEKFCFEFTGDVDGKRYVTQTNLTVVAPTL  100
                  |.:.:|.::|||||||||.|||||.|.|.....|||:|.|.||||||||
SEQ ID NO. 3   51 LNESDKQAISFDFVAPELKQDEKYCFTFKGITGDHRYITNTTLTVVAPTL  100

SEQ ID NO. 1  101 EVYVDHASLPSLQQLMKIIQQKNEYSQNERFISWGRIGLTEDNAEKLNAH  150
                  |||:|||||||||||:.|||.|:||..|:||:||.|:.:...|||.|||.|
SEQ ID NO. 3  101 EVYIDHASLPSLQQLIHIIQAKDEYPSNQRFVSWKRVTVDADNANKLNIH  150

SEQ ID NO. 1  151 IYPLAGNNTSQELVDAVIDYADSKNRLNLELNTNTAHSFPNLAPILRIIS  200
                  .|||.|||||.|:.|.:..:|.||||||:|..|||||.|.||.||.|::.:.
SEQ ID NO. 3  151 TYPLKGNNTSPEMVAAIDEYAQSKNRLNIEFYTNTAHVFNNLPPIIQPLY  200

SEQ ID NO. 1  201 SKSNILISNINLYDDGSAEYVNLYNWKDTEDKSVKLSDSFLVLKDYFNGI  250
                  :....:.||:|:|||||:|||:||.||||.:|...|......:|.:|..|.
SEQ ID NO. 3  201 NNEKVKISHISLYDDGSSEYVSLYQWKDTPNKIETLEGEVSLLANYLAGT  250

SEQ ID NO. 1  251 SSEKPSGIYGRYNWHQLYNTSYYFLRKDYLTVEPQLHDLREYLGGSLKQM  300
                  |.:.|.|:..|||||:||:|.|||||:|||.||..|||||:|||.|.|||
SEQ ID NO. 3  251 SPDAPKGMGNRYNWHKLYDTDYYFLREDYLDVEANLHDLRDYLGSSAKQM  300

SEQ ID NO. 1  301 SWDGFSQLSKGDKELFLNIVGFDQEKLQQEYQQSELPNFVFTGTTTWAGG  350
                  .||.|::||...:.|||:|||||||:.||.||||:||||||||||||
SEQ ID NO. 3  301 PWDEFAKLSDSQQTLFLDIVGFDKEQLQQQYSQSPLPNFIFTGTTTWAGG  350

SEQ ID NO. 1  351 ETKEYYAQQQVNVVNNAINETSPYYLGREHDLFFKGHPRGGIINDIILGS  400
                  |||||||||||||:|||||||||||||:::||||||||.|::|||||||
SEQ ID NO. 3  351 ETKEYYAQQQVNVINNAINETSPYYLGKDYDLFFKGHPAGGVINDIILGS  400

SEQ ID NO. 1  401 FNNMIDIPAKVSFEVLMMTGMLPDTVGGIASSLYFSIPAEKVSFIVFTSS  450
                  |.:||:||||:|||||||||.||||||.|||||||:|||:|:|||||||
SEQ ID NO. 3  401 FPDMINIPAKISFEVLMMTDMLPDTVAGIASSLYFTIPADKVNFIVFTSS  450

SEQ ID NO. 1  451 DTITDREDALKSPLVQVMMTLGIVKEKDVLFWSDLPDCSSGVCIAQY----  497
                  ||||||:||||||||||||:|||||||||||:....|..|.|.:.
SEQ ID NO. 3  451 DTITDREEALKSPLVQVMLTLGIVKEKDVLFWADHKVNSMEVAIDEACTR  500

SEQ ID NO. 1  498 ---------------------------------------------------  497

SEQ ID NO. 3  501 IIAKRQPTASDLRLVIAIIKTITDLERIGDVAESIAKVALESFSNKQYNL  550

SEQ ID NO. 1  498 ---------------------------------------------------  497

SEQ ID NO. 3  551 LVSLESLGQHTVRMLHEVLDAFARMDVKAAIEVYQEDDRIDQEYESIVRQ  600

SEQ ID NO. 1  498 ---------------------------------------------------  497

SEQ ID NO. 3  601 LMAHMMEDPSSIPNVMKVMWAARSIERVGDRCQNICEYIIYFVKGKDVRH  650

SEQ ID NO. 1  498 ------------    497

SEQ ID NO. 3  651 TKPDDFGTMLD     661
```

Figure 3.

TERNARY MIXTURES OF 6'-SL, LNNT AND LST C

CROSS-REFERENCE TO RELATED APPLICATIONS

This is a national stage filing in accordance with 35 U.S.C. § 371 of PCT/IB2016/053412, filed Jun. 9, 2016, which claims the benefit of the priority of European Patent Application EP 15171177.7 filed Jun. 9, 2015, the contents of each are incorporated herein by reference.

Sequence Listing

This instant application contains a Sequence Listing which has been submitted in ASCII format via EFS-Web and is hereby incorporated by reference in its entirety. Said ASCII copy, created on Dec. 4, 2017, is named 089US00_029037-8018_SequenceListing.txt, and is 14,059 bytes in size.

FIELD OF THE INVENTION

The present invention relates to ternary mixtures of human milk oligosaccharides (HMOs), particularly mixtures of 6'-O-sialyllactose (6'-SL), lacto-N-neotetraose (LNnT) and sialyllacto-N-tetraose c (LST c), a process for making the ternary mixtures, and applications of the ternary mixtures in human health.

BACKGROUND OF THE INVENTION

HMOs have become the subject of much interest in recent years due to their roles in numerous biological processes occurring in the human organism. Mammalian milk contains at least 130 of these complex oligosaccharides (Urashima et al: *Milk Oligosaccharides*, Nova Biomedical Books, New York, 2011, ISBN: 978-1-61122-831-1).

Previously, the only source of HMOs had been mammalian milk which contains mostly water, together with 55-70 g/l lactose, 24-59 g/l lipids, ca. 13 g/l proteins, 5-15 g/l HMOs and ca. 1.5 g/l minerals.

However, efforts to develop processes for synthesizing these oligosaccharides have increased significantly in the last ten years due to their roles in numerous human biological processes. In this regard, processes have been developed for producing HMOs by microbial fermentations, enzymatic processes, chemical syntheses, or combinations of these technologies. For example, by chemical processes, LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, and 6'-SL and salts thereof can be made as described in WO 2010/100979. As examples of biotechnological processes, WO 01/04341 and WO 2007/101862 describe how to make core human milk oligosaccharides optionally substituted by fucose or sialic acid using genetically modified *E. coli*. As an example of enzymatic processes, sialylated oligosaccharides can be made as described in EP-A-577580.

Efforts have also been made to develop processes for synthesizing enzymatically mixtures of HMO oligosaccharides, without having to synthesize all of the component oligosaccharides of the mixture as described in WO 2012/156897 and WO 2012/156898. Such processes have provided reaction mixtures containing a plurality of different oligosaccharides.

However, better processes have been sought for the synthesis of mixtures of HMOs, especially mixtures consisting of three HMOs, particularly 6'-SL, LNnT and LST c.

Evidence is accumulating that the resident community of microbes, called the microbiome, in the human digestive tract plays a major role in health and disease. When the normal composition of the microbiome is thrown off balance, the human host can suffer consequences. Recent research has implicated microbiome imbalances in disorders as diverse as cancer, obesity, inflammatory bowel disease, psoriasis, asthma, and possibly even autism. HMOs are believed to positively modulate the microbiome, and they are of increasing interest for this purpose. However, the remarkable diversity of HMOs, coupled with their lack of availability, has hampered studies of the specific functions of individual HMOs. There is a clear need for specific HMOs or combinations of HMOs to modulate the microbiome in a desired manner, so as to address specific human health issues.

SUMMARY OF THE INVENTION

A first aspect of this invention relates to a first mixture of HMOs consisting essentially of 6'-O-sialyllactose (6'-SL), lacto-N-neotetraose (LNnT) and sialyllacto-N-tetraose c (LST c). Advantageously in this first HMO mixture, the molar ratio of LST c relative to (6'-SL+LNnT) is at least 1:18, advantageously at least 1:8, more advantageously at least 1:5, even more advantageously at least 1:3. Also advantageously in the first mixture, the molar ratio of 6'-SL relative to LNnT is 0.18-5.5, more advantageously 0.3-3, still more advantageously about 1.

A second aspect of this invention relates to a process for making the first HMO mixture by reacting a 6'-SL donor and an LNnT acceptor in the presence of an α2,6-transsialidase and then removing lactose and the α2,6-transsialidase from the reaction medium. Advantageously, the process involves the use 6'-SL and LNnT in a molar ratio of 1:3 to 3:1, advantageously 1:2 to 2:1, more advantageously 1:1, with an α2,6-transsialidase having a conversion rate of at least 20% up to 55%, advantageously at least 30%, more advantageously at least 40%, even more advantageously at least 45%, for the reaction of 6'-SL and LNnT.

A third aspect of this invention relates to a second mixture of HMOs which consists essentially of 6'-SL, LNnT, LST c and lactose. Advantageously in this second mixture:
  the molar ratio of (6'-SL+LNnT) relative to LST c is 2-18 and
  the molar ratio of lactose relative to LST c is about 1.
More advantageously, one of the molar ratios 6'-SL to LST c and LNnT to LST c is not more than 4. Even more advantageously, the second HMO mixture has a molar ratio of 6'-SL to LNnT of 0.18-5.5.

A fourth aspect of this invention relates to a process for making the second HMO mixture by reacting a 6'-SL donor and an LNnT acceptor in the presence of an α2,6-transsialidase, and then removing the α2,6-transsialidase from the reaction medium. The resulting reaction mixture is a second HMO mixture of this invention.

A fifth aspect of this invention relates to an anti-infective composition for treating viral and/or bacterial infections comprising 6'-SL, LNnT and LST c. This composition contains a mixture of a plurality of different HMOs with novel properties and biological activities. Specifically, the composition increases *Bifidobacterium* abundance of the microbiome in a human. Further, the composition inhibits pathogen binding, and thereby protects the host from infection, especially infections of the respiratory tract. The composition can also be used to treat and/or reduce the risk of a broad range of viral and/or bacterial infections of a human, especially infections of the respiratory tract. The anti-infective composition is advantageously the first or second mixture of this invention, more advantageously the first mixture, as described above.

A sixth aspect of this invention relates to a method of modulating the microbiome of a human, in particular a non-infant individual, to increase *Bifidobacterium* abundance. The method comprises administering, to said human, 6'-SL, LNnT and LST c, advantageously the first or second mixture of this invention, more advantageously the first mixture, as described above.

A seventh aspect of this invention relates to a method of preventing or treating viral and/or bacterial infections, especially infections of the respiratory tract, in a human, in particular a non-infant individual. The method comprises administering, to the human, a mixture of 6'-SL, LNnT and LST c, advantageously the first or second mixture of this invention, more advantageously the first mixture, as described above.

BRIEF DESCRIPTION OF THE FIGURES

The following figures are intended to illustrate the invention further. They are not intended to limit the subject matter of the invention.

FIG. 1: shows the sequences and alignment of 3 α2,6-sialyl transferases: *P. leiognathi* JT-SHIZ-119 sialyl transferase truncated by its signal peptide (Δ2-15) (SEQ ID No. 1), *P. leiognathi* JT-SHIZ-145 sialyl transferase truncated by its signal peptide (Δ2-15) (SEQ ID No. 2) and *P. damselae* JT0160 sialyl transferase truncated by its signal peptide (Δ2-15) (SEQ ID No. 3). Sequences were aligned by Multiple Sequence Alignment (MSA) using CLUSTAL Omega (1.2.1) (http://www.ebi.ac.uk/Tools/msa/clustalo/).

FIG. 2: shows the sequences and alignment of 2 α2,6-sialyl transferases: *P. leiognathi* JT-SHIZ-119 sialyl transferase truncated by its signal peptide (Δ2-15) (being SEQ ID No. 1) and *P. leiognathi* JT-SHIZ-145 sialyl transferase truncated by its signal peptide (Δ2-15) (SEQ ID No. 2). The sequences were aligned by Pairwise Sequence Alignment using EMBOSS Needle (http://www.ebi.ac.uk/Tools/psa/emboss_needle/).

FIG. 3: shows the sequences and alignment of 2 α2,6-sialyl transferases: *P. leiognathi* JT-SHIZ-119 sialyl transferase truncated by its signal peptide (Δ2-15) (being SEQ ID No. 1) and *P. damselae* JT0160 sialyl transferase truncated by its signal peptide (Δ2-15) (SEQ ID No. 3). The sequences were aligned by Pairwise Sequence Alignment using EMBOSS Needle (http://www.ebi.ac.uk/Tools/psa/emboss_needle/).

DETAILED DESCRIPTION OF THE INVENTION

In accordance with this invention, it has been surprisingly discovered that a mixture of 6'-SL, LNnT and LST c possess an anti-infective activity and therefore can be used as an anti-infective composition, e.g. for treating bacterial infections through specific modulation of the microbiome and by preventing binding of pathogens to epithelial cells. The mixture increases *Bifidobacterium* abundance of the microbiome. The mixture also reduces *Firmicutes* abundance of the microbiome, especially *Clostridia* species. The mixture also binds a range of respiratory pathogens which inhibits binding of these pathogens to the epithelial cells. In this way, the mixture provides a form of protection against infections, especially infections of the respiratory tract.

The present invention relates to synthetic HMO mixtures. The term "synthetic mixture" or "synthetic composition" designates a mixture or composition which is artificially prepared and preferably mean a mixture or composition containing at least one compound that is produced ex vivo chemically and/or biologically, e.g. by means of chemical reaction, enzymatic reaction or recombinantly. In this regard, "synthetic" is used as opposite to "natural", and means that a synthetic mixture or composition of the invention is not identical to a natural composition or mixture, like human milk, or at least one HMO of the mixture or the composition is not originated from a natural source, like e.g. human milk.

The First HMO Mixture and its Production

The mixture of this invention can be a first mixture of HMOs consisting essentially of 6'-SL, LNnT and LST c. The molar ratio of HMOs in the first mixture may vary. In one embodiment, the molar ratio of LST c relative to a combination 6'-SL+LNnT is at least 1:18. In another embodiment, this ratio may be at least 1:8. Certain ratios of LST c relative to a combination 6'-SL+LNnT in the first mixture, such as at least 1:5 or at least 1:3, may be preferred in some embodiments. In some other embodiments the first HMO mixture may have a molar ratio of 6'-SL relative to LNnT of 0.18-5.5 or 0.3-3, preferably about 1.

The first HMO mixture can be readily obtained by a process, which involves treating a 6'-SL donor and an LNnT acceptor, with an α2,6-transsialidase and then removing lactose and the α2,6-transsialidase from the reaction medium. In one embodiment, this process comprises the step of contacting 6'-SL and LNnT in a molar ratio of preferably 1:3 to 3:1 or 1:2 to 2:1, such as around 1:1, with an α2,6-transsialidase having a conversion rate for the reaction 6'-SL and LNnT of at least 20%, up to about 55%, preferably at least 30% such as from at least 30% to about 50%, at least 40% or at least 45%. The reaction mixture, so-produced, containing LST c, lactose, unreacted 6'-SL, LNnT and α2,6-transsialidase, is then subjected to conventional purification steps to remove substances other than 6'-SL, LNnT and LST c, i.e. α2,6-transsialidase and lactose. If the mixture is obtained by an in situ enzymatic reaction, the α2,6-transsialidase can be inactivated and removed, e.g. by denaturation followed by centrifugation or ultrafiltration, to produce a mixture consisting essentially of 6'-SL, LNnT, LST c and lactose. The lactose in this mixture can then be separated from the 6'-SL, LNnT and LST c e.g. by cascade ultra- and/or nanofiltration, or the lactose can first be treated with lactase to degrade it to glucose and galactose which can then be separated from the 6'-SL, LNnT and LST c by ultra- and/or nanofiltration. In case of producing the mixture containing LST c, lactose, unreacted 6'-SL, LNnT and α2,6-transsialidase recombinantly, i.e. by a fermentation process using a genetically modified microorganism, such as a bacterium, expressing a recombinant α2,6-transsialidase, the purification of the HMO mixture may be done using steps of removal of the cell material from the fermentation broth followed by removing non-carbohydrate particulates and contaminants like salts, charged molecules, proteins, DNA, colorizing/caramel bodies, etc., to produce a mixture consisting essentially of 3'-SL, 3-FL, FSL and lactose. Separation of lactose can be conducted as described above.

The Second HMO Mixture and its Production

The mixture of this invention can also be a second mixture of HMOs which consists essentially of 6'-SL, LNnT, LST c and lactose. Preferably, in this second mixture:

the molar ratio of (6'-SL+LNnT) relative to LST c is 2-18, and the molar ratio of lactose relative to LST c is about 1.

More preferably, one of the molar ratios 6'-SL to LST c and LNnT to LST c is not more than 4.

The second HMO mixture of the invention can be obtained by carrying out the process as described above, which does not comprise a step of removing lactose from the obtained HMO mixtures. In one embodiment, 6'-SL and LNnT are reacted in a molar ratio of preferably 1:3 to 3:1, more preferably 1:2 to 2:1, even more preferably 1:1, with an α2,6-transsialidase wherein the conversion rate is at least 20%, advantageously at least 30%, more advantageously at least 40%, even more advantageously at least 45%. Preferably, in the resulting second HMO mixture, the molar ratio of 6'-SL to LNnT is 0.3-3.

Embodiments of the First and the Second HMO Mixtures

When the process of this invention is carried out with a molar ratio of 6'-SL to LNnT of 2:1 to 1:2 and a conversion rate of 20-50%, a first or a second HMO mixture having a molar ratio of (6'-SL+LNnT) to LST c of 2-13 and a molar ratio of 6'-SL to LNnT of 0.33-3 can be made.

When the process is carried out with a molar ratio of 6'-SL to LNnT of 1:1 and a conversion rate of 20-45%, a first or a second HMO mixture having a molar ratio of (6'-SL+LNnT) to LST c of 2.44-8 and a molar ratio of 6'-SL to LNnT of 1 can be made.

When the process is carried out with a molar ratio of 6'-SL to LNnT of 3:1 to 1:3 and a conversion rate of 30-50%, a first or a second HMO mixture having a molar ratio of (6'-SL+LNnT) to LST c of 2-12 and a molar ratio of 6'-SL to LNnT of 0.2-5 can be made.

When the process is carried out with a molar ratio of 6'-SL to LNnT of 2:1 to 1:2 and a conversion rate of 30-50%, a first or a second HMO mixture having a molar ratio of (6'-SL+LNnT) to LST c of 2-8 and a molar ratio of 6'-SL to LNnT of 0.33-3 can be made.

When the process is carried out with a molar ratio of 6'-SL to LNnT of 1:1 and a conversion rate of 30-45%, a first or a second HMO mixture having a molar ratio of (6'-SL+LNnT) to LST c of 2.44-5 and a molar ratio of 6'-SL to LNnT of 1 can be made.

When the process is carried out with a molar ratio of 6'-SL to LNnT of 3:1 to 1:3 and a conversion rate of 25-35%, a first or a second HMO mixture having a molar ratio of (6'-SL+LNnT) to LST c of 3.7-14 and a molar ratio of 6'-SL to LNnT of 0.25-4.1 can be made.

When the process is carried out with a molar ratio of 6'-SL to LNnT of 2:1 to 1:2 and a conversion rate of 25-35%, a first or a second HMO mixture having a molar ratio of (6'-SL+LNnT) to LST c of 3.7-10 and a molar ratio of 6'-SL to LNnT of 0.39-2.54 can be made.

When the process is carried out with a molar ratio of 6'-SL to LNnT of 1:1 and a conversion rate of 25-35%, a first or a second HMO mixture having a molar ratio of (6'-SL+LNnT) to LST c of 3.7-6 and a molar ratio of 6'-SL to LNnT of 1 can be made.

When the process is carried out with a molar ratio of 6'-SL to LNnT of 3:1 to 2:1 and a conversion rate of 30-50%, a first or a second HMO mixture having a molar ratio of (6'-SL+LNnT) to LST c of 4-12 and a molar ratio of 6'-SL to LNnT of 2.43-5 can be made.

When the process is carried out with a molar ratio of 6'-SL to LNnT of 2:1 to 1:1 and a conversion rate of 20-45%, a first or a second HMO mixture having a molar ratio of (6'-SL+LNnT) to LST c of 2.44-13 and a molar ratio of 6'-SL to LNnT of 1-2.82 can be made.

When the process is carried out with a molar ratio of 6'-SL to LNnT of 1:1 to 1:2 and a conversion rate of 20-45%, a first or a second HMO mixture having a molar ratio of (6'-SL+LNnT) to LST c of 2.44-13 and a molar ratio of 6'-SL to LNnT of 0.35-1 can be made.

When the process is carried out with a molar ratio of 6'-SL to LNnT of 1:2 to 1:3 and a conversion rate of 30-50%, a first or a second HMO mixture having a molar ratio of (6'-SL+LNnT) to LST c of 4-12 and a molar ratio of 6'-SL to LNnT of 0.20-0.41 can be made.

Enzymatic Production of the HMO Mixtures of the Invention

In accordance with this invention, the term "α2,6-transsialidase" means any wild type or engineered sialidase that is able to transfer a sialyl residue to the 6-position of a, preferably terminal, galactose unit in an oligosaccharide acceptor. In order to make the first or the second HMO mixtures the α2,6-transsialidase should be regioselective with regard to the LNnT acceptor since it contains two galactosyl units. The α2,6-transsialidases used for this purpose shall be regioselective to the terminal galactosyl residue of the LNnT, that is the formation of LST c (depicted as compound A) is preferred over that of compound B and/or compound C (see Scheme 1). Thus when employing a regioselective α2,6-transsialidase, the reaction should be stopped before there is significant by-product formation. This time point can be easily determined by well-known enzyme kinetic measurements and in case of the most specific enzymes no by-products can be observed even at 45% of conversion when 6'-SL and LNnT are employed in equimolar ratio. The conversion without by-product occurrence may be higher when either 6'-SL or LNnT is used in excess.

Scheme 1
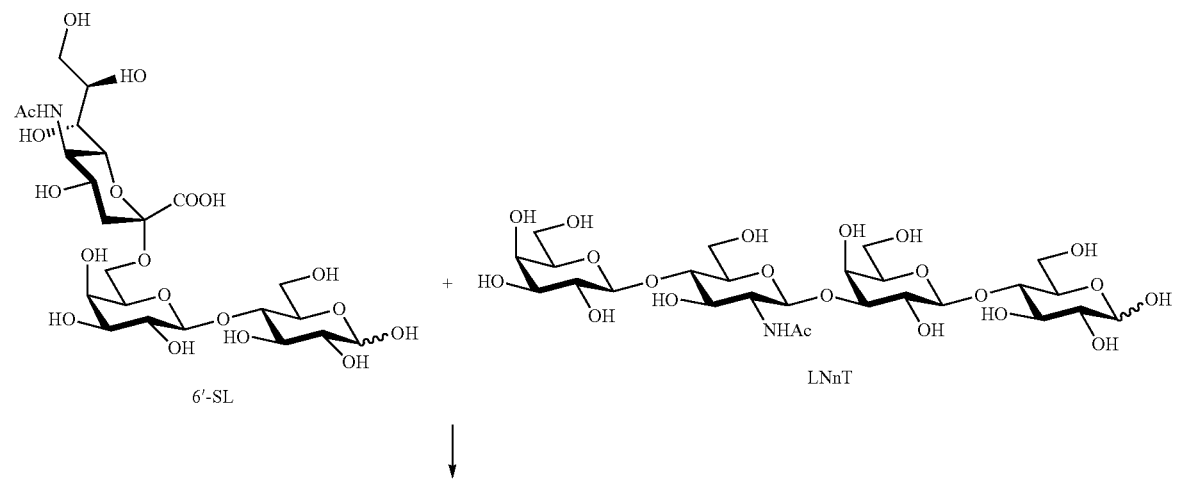
6'-SL + LNnT
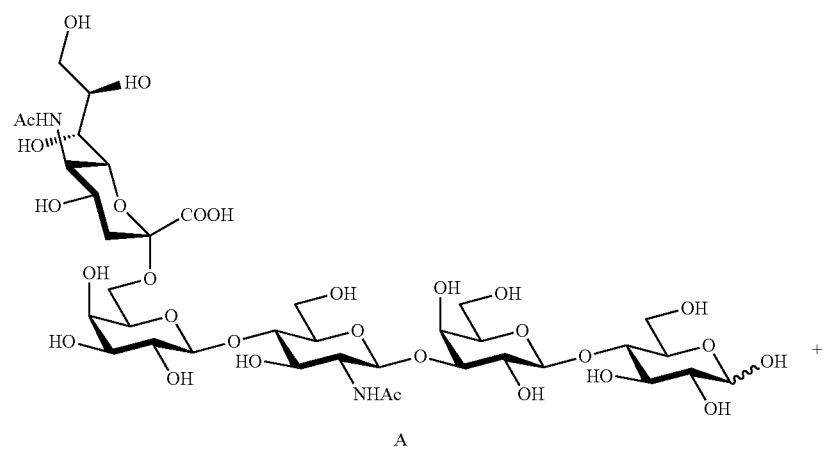
A
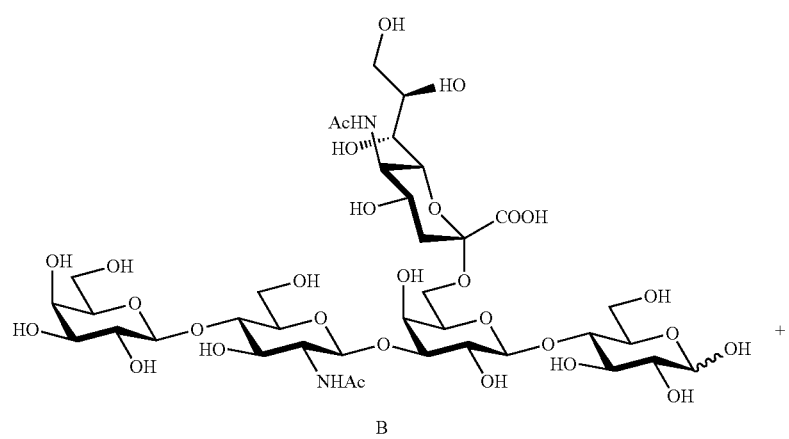
B

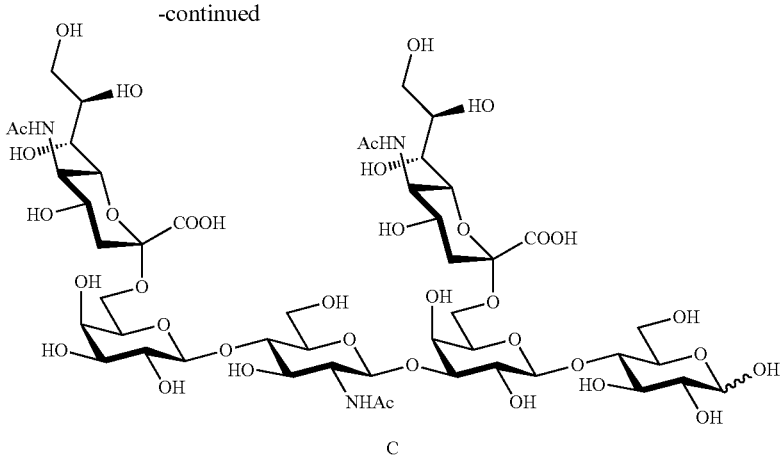

C

The α2,6-transsialidase used in making the HMO mixtures of this invention can be any wild type enzyme having α2,6-transsialidase activity, such as an α2,6-sialyl transferase from S Photobacterium damselae JT0160 (U.S. Pat. Nos. 5,827,714, 6,255,094, Yamamoto et al. *J. Biochem.* 123, 94 (1998)), Photobacterium sp. JT-ISH-224 (U.S. Pat. Nos. 7,993,875, 8,187,838, Tsukamoto et al. *J. Biochem.* 143, 187 (2008)) P. leiognathi JT-SHIZ-145 (U.S. Pat. Nos. 8,187,853, 8,372,617, Yamamoto et al. *Glycobiology* 17, 1167 (2007)) or P. leiognathi JT-SHIZ-119 (US 2012/184016, Mine et al. *Glycobiology* 20, 158 (2010)).

The α2,6-transsialidase used in making the HMO mixtures of this invention preferably has an amino acid sequence that is substantially identical with the amino acid sequence of SEQ ID No. 1, and which comprises at least one of:
- at position 156, an amino acid selected from Ser, Thr, Cys, Tyr, Asn, Gln or Trp, preferably Ser, Cys or Tyr; and/or
- at position 161, an amino acid selected from Ala, Val, Ile, Leu, Phe, Tyr, Trp or Gly, preferably Phe or Gly; and/or
- at position 180, an amino acid selected from Asp, Asn, Gln, preferably Asp; and/or
- at position 186, an amino acid selected from Val, Ile, Leu, Met, Phe, Tyr, Trp, Ser, Cys or Thr, preferably Tyr, Cys or Leu; and/or
- at position 218, an amino acid selected from Val, Ile, Leu, Met, Phe, Tyr, Trp, Cys, Gly or Thr, preferably Ile, Val, Phe or Tyr; and/or
- at position 222, an amino acid selected from Gln, Asp, Glu, Cys, Thr, Phe, Tyr, Trp, Arg, Lys or His, preferably Cys, Asp, Arg or Phe; and/or
- at position 235, an amino acid selected from Arg, His, Ser, Cys, Ala, Val, Ile or Leu, preferably Arg, His, Cys or Val; and/or
- at position 242, an amino acid selected from Arg, His or Lys, preferably His; and/or
- at position 261, an amino acid selected from His, Lys, Asp, Glu, Ala, Val, Leu or Phe, preferably Asp, Phe, His or Val; and/or
- at position 315, an amino acid selected from Ser, Thr or Cys, preferably Cys; and/or
- at position 342, an amino acid selected from Ser or Cys, preferably Cys; and/or
- at position 349, an amino acid selected from Ser, Thr or Cys, preferably Ser or Cys; and/or
- at position 350, an amino acid selected from Ser, Thr, Cys, Tyr, Trp or Phe, preferably Ser, Tyr, Phe or Cys; and/or
- at position 356, an amino acid selected from Ala, Val, Ile, Leu, Phe or Trp, preferably Val or Phe; and/or
- at position 438, an amino acid selected from Arg, His or Lys, preferably His; wherein said positions are defined by alignment of said amino acid sequence with SEQ ID No. 1 using a comparison algorithm.

Accordingly, the α2,6-transsialidase used in making the HMO mixtures of this invention is preferably a mutated α2,6-transsialidase having an amino acid sequence which is substantially identical with SEQ ID No. 1 (i.e. has at least 60 percent (%) identity with the amino acid sequence of SEQ ID No. 1) and has been mutated (i.e. one amino acid has been replaced by another amino acid) at one or more amino acid positions (numbering corresponding to alignment of the amino acid sequence with SEQ ID No. 1) as follows:
- 156 which is substituted by Ser, Thr, Cys, Tyr, Asn, Gln or Trp, preferably Ser, Cys or Tyr;
- 161 which is substituted by Ala, Val, Ile, Leu, Phe, Tyr, Trp or Gly, preferably Phe or Gly;
- 180 which is substituted by Asp, Asn, Gln, preferably Asp;
- 186 which is substituted by Val, Ile, Leu, Met, Phe, Tyr, Trp, Ser, Cys or Thr, preferably Tyr, Cys or Leu;
- 218 which is substituted by Val, Ile, Leu, Met, Phe, Tyr, Trp, Cys, Gly or Thr, preferably Ile, Val, Phe or Tyr;
- 222 which is substituted by Gln, Asp, Glu, Cys, Thr, Phe, Tyr, Trp, Arg, Lys or His, preferably Cys, Asp, Arg or Phe;
- 235 which is substituted by Arg, His, Ser, Cys, Ala, Val, Ile or Leu, preferably Arg, His, Cys or Val;
- 242 which is substituted by Arg, His or Lys, preferably His;
- 261 which is substituted by His, Lys, Asp, Glu, Ala, Val, Leu or Phe, preferably Asp, Phe, His or Val;
- 315 which is substituted by Ser, Thr or Cys, preferably Cys;
- 342 which is substituted by Ser or Cys, preferably Cys;
- 349 which is substituted by Ser, Thr or Cys, preferably Ser or Cys;
- 350 which is substituted by Ser, Thr, Cys, Tyr, Trp or Phe, preferably Ser, Tyr, Phe or Cys;
- 356 which is substituted by Ala, Val, Ile, Leu, Phe or Trp, preferably Val or Phe; or
- 438 which is substituted by Arg, His or Lys, preferably His.

The amino acid sequence of SEQ ID No. 1 corresponds to the amino acid sequence of the *P. leiognathi* JT-SHIZ-119 sialyl transferase truncated by its signal peptide (Δ2-15).

The mutated α2,6-transsialidases defined above show improved regioselectivity in comparison with the wild-type (non-mutated) parent enzyme having an identical amino acid sequence with that of SEQ ID No. 1 or other corresponding wild-type (non-mutated) enzymes having an amino acid sequence which is substantially identical with SEQ ID No. 1, and from which wild-type enzymes the mutants stem.

Furthermore, the mutated α2,6-transsialidases according to the invention show not only a transsialidase, preferably an α2,6-transsialidase, activity but a sialyl transferase, preferably an α2,6-sialyl transferase, activity too.

In accordance with this invention, the terms "substantial identity" and "substantially identical" in the context of two or more nucleic acid or amino acid sequences preferably mean that the two or more sequences are the same or have at least about 60% of nucleotides or amino acid residues in common when compared and aligned for maximum correspondence over a comparison window or designated sequences of nucleic acids or amino acids (i.e. the sequences have at least about 60 percent (%) identity). Percent identity of nucleic acid or amino acid sequences can be measured using a BLAST 2.0 sequence comparison algorithms with default parameters, or by manual alignment and visual inspection (see e.g. http://www.ncbi.nlm.nih.gov/BLAST/). In accordance with this invention, the percent identity of either: i) a polypeptide fragment that is "substantially identical" with a polypeptide of SEQ ID No. 1 or ii) a nucleic acid sequence that encodes a polypeptide fragment and that is "substantially identical" with a nucleic acid sequence encoding a polypeptide of SEQ ID No. 1 is preferably at least 65%, more preferably at least 70%, still more preferably at least 75%, even more preferably at least 80%, yet more preferably at least 85%, still even more preferably at least 90%, yet even more preferably at least 92%, especially at least 93%, more especially at least 94%, even more especially at least 95%, yet even more especially at least 96%, particularly at least 97%, more particularly at least 98%, and most particularly at least 99% identical to SEQ ID No. 1. This definition also applies to the compliment of a test sequence and to sequences that have deletions and/or additions, as well as those that have substitutions. In this regard, the position of a mutation in the amino acid sequence of the novel engineered (mutated) transsialidases of the invention with reference to SEQ ID No. 1 means that the position is defined by alignment of the test transsialidase sequence with SEQ ID No. 1 using either a protein sequence comparison algorithm or by manual alignment and visual inspection mentioned above. Examples of such aligned sequences are shown in FIG. 1-3. An example of an algorithm that is suitable for determining percent identity, sequence similarity and making alignment is the BLAST 2.2.20+ algorithm, which is described in Altschul et al. *Nucl. Acids Res.* 25, 3389 (1997). BLAST 2.2.20+ is used to determine percent sequence identity for the nucleic acids and proteins of the invention. Software for performing BLAST analyses is publicly available through the National Center for Biotechnology Information (http://www.ncbi.nlm.nih.gov/).

Examples of sequence alignment algorithms are CLUSTAL Omega (http://www.ebi.ac.uk/Tools/msa/clustalo/), EMBOSS Needle (http://www.ebi.ac.uk/Tools/psa/emboss_needle/), MAFFT (http://mafft.cbrc.jp/alignment/server/) or MUSCLE (http://www.ebi.ac.uk/Tools/msa/muscle/).

The preferred wild type α2,6-sialyl transferases with a substantially identical amino acid sequence with SEQ ID No. 1, that is having at least about 60 percent sequence identity (determined by BLAST) with SEQ ID No. 1, are listed in Table 1.

TABLE 1

| Description | Identity | Accession Number |
|---|---|---|
| α2,6-sialyl transferase [*Photobacterium leiognathi*] | 100% | BAI49484.1 |
| α2,6-sialyl transferase [*Photobacterium leiognathi*] | 96% | BAF91416.1 |
| Chain A, crystal structure of sialyl transferase from *Photobacterium damselae*, residues 113-497 | 70% | 4R9V_A |
| sialyl transferase 0160 [*Photobacterium damselae*] | 68% | WP_005298232.1 |
| Chain A, crystal structure of sialyl transferase from *Photobacterium damselae* | 67% | 4R83_A |
| sialyl transferase 0160 [*Photobacterium damselae*] | 66% | BAA25316.1 |

Preferably, α2,6-sialyl transferases with a substantially identical amino acid sequence with SEQ ID No. 1 that can be mutated to have an α2,6-transsialidase activity with improved regioselectivity, are the sialyl transferase from *P. leiognathi* JT-SHIZ-119 or its Δ2-15 truncated variant, the sialyl transferase from *P. leiognathi* JT-SHIZ-145 or its Δ2-15 truncated variant, or the sialyl transferase from *P. damselae* JT0160 or its Δ2-15 truncated variant, more preferably the sialyl transferase from *P. leiognathi* JT-SHIZ-119 or its Δ2-15 truncated variant.

In the mutated α2,6-transsialidase used in making the HMO mixtures of this invention, the amino acid sequence which is substantially identical with the amino acid sequence of SEQ ID No. 1 is preferably the sialyl transferase from *P. leiognathi* JT-SHIZ-119 or its Δ2-15 truncated variant, the sialyl transferase from *P. leiognathi* JT-SHIZ-145 or its Δ2-15 truncated variant, or the sialyl transferase from *P. damselae* JT0160 or its Δ2-15 truncated variant, and has the following mutations (numbering corresponding to alignment of the amino acid sequence with SEQ ID No. 1):

at position 156 Gly is substituted by Ser, Thr, Cys, Tyr, Asn, Gln or Trp, preferably Ser, Cys or Tyr; and/or at position 161 Gln or Pro is substituted by Ala, Val, Ile, Leu, Phe, Tyr, Trp or Gly, preferably Phe or Gly; and/or at position 180 Glu is substituted by Asp, Asn, Gln, preferably Asp, and/or at position 186 Ala or Gly is substituted by Val, Ile, Leu, Met, Phe, Tyr, Trp, Ser, Cys or Thr, preferably Tyr, Cys or Leu; and/or at position 218 Ala or Ser is substituted by Val, Ile, Leu, Met, Phe, Tyr, Trp, Cys, Gly or Thr, preferably Ile, Val, Phe or Tyr; and/or at position 222 Asn or Ser is substituted by Gln, Asp, Glu, Cys, Thr, Phe, Tyr, Trp, Arg, Lys or His, preferably Cys, Asp, Arg or Phe; and/or at position 235 Lys or Thr is substituted by Arg, His, Ser, Cys, Ala, Val, Ile or Leu, preferably Arg, His, Cys or Val; and/or at position 242 Val or Leu is substituted by Arg, His or Lys, preferably His; and/or at position 261 Arg or Ile is substituted by His, Lys, Asp, Glu, Ala, Val, Leu or Phe, preferably Asp, Phe, His or Val; and/or at position 315 Leu is substituted by Ser, Thr or Cys, preferably Cys; and/or at position 342 Thr is substituted by Ser or Cys, preferably Cys; and/or at position 349 Gly is substituted by Ser, Thr or Cys, preferably Ser or Cys; and/or at position 350 Gly is substituted by Ser, Thr, Cys, Tyr, Trp or Phe, preferably Ser, Tyr, Phe or Cys; and/or at position 356 Tyr is substituted by Ala, Val, Ile, Leu, Phe or Trp, preferably Val or Phe; and/or at position 438 Pro is substituted by Arg, His or Lys, preferably His.

Preferably, in the mutated α2,6-transsialidase, the amino acid sequence which is substantially identical with the amino acid sequence of SEQ ID No. 1 is an amino acid sequence which is at least 90% identical with the amino acid sequence of SEQ ID No. 1, more preferably the amino acid sequence of the sialyl transferase from *P. leiognathi* JT-SHIZ-119 or its Δ2-15 truncated variant, or the sialyl transferase from *P. leiognathi* JT-SHIZ-145 or its Δ2-15 truncated variant, particularly the sialyl transferase from *P. leiognathi* JT-SHIZ-119 or its Δ2-15 truncated variant, and comprises mutation(s) at the following amino acid positions (numbering corresponding to alignment of the amino acid sequence with SEQ ID No. 1):

at position 156 Gly is substituted by Ser, Thr, Cys, Tyr, Asn, Gln or Trp, preferably Ser, Cys or Tyr; and/or at position 161 Gln is substituted by Ala, Val, Ile, Leu, Phe, Tyr, Trp or Gly, preferably Phe or Gly; and/or at position 180 Glu is substituted by Asp, Asn, Gin, preferably Asp, and/or at position 186 Ala or Gly is substituted by Val, Ile, Leu, Met, Phe, Tyr, Trp, Ser, Cys, or Thr, preferably Tyr, Cys or Leu; and/or at position 218 Ala is substituted by Val, Ile, Leu, Met, Phe, Tyr, Trp, Cys, Gly or Thr, preferably Ile, Val, Phe or Tyr; and/or at position 222 Asn or Ser is substituted by Gin, Asp, Glu, Cys, Thr, Phe, Tyr, Trp, Arg, Lys or His, preferably Cys, Asp, Arg or Phe; and/or at position 235 Lys is substituted by Arg, His, Ser, Cys, Ala, Val, Ile or Leu, preferably Arg, His, Cys or Val; and/or at position 242 Val is substituted by Arg, His or Lys, preferably His; and/or at position 261 Arg or Ile is substituted by His, Lys, Asp, Glu, Ala, Val, Leu or Phe, preferably Asp, Phe, His or Val; and/or at position 315 Leu is substituted by Ser, Thr or Cys, preferably Cys; and/or at position 342 Thr is substituted by Ser or Cys, preferably Cys; and/or at position 349 Gly is substituted by Ser, Thr or Cys, preferably Ser or Cys; and/or at position 350 Gly is substituted by Ser, Thr, Cys, Tyr, Trp or Phe, preferably Ser, Tyr, Phe or Cys; and/or at position 356 Tyr is substituted by Ala, Val, Ile, Leu, Phe or Trp, preferably Val or Phe; and/or at position 438 Pro is substituted by Arg, His or Lys, preferably His.

More preferably, in the mutated α2,6-transsialidase, the amino acid sequence which is at least 90% identical with the amino acid sequence of SEQ ID No. 1 is the sialyl transferase from *P. leiognathi* JT-SHIZ-119 or its Δ2-15 truncated variant, which is mutated at the following amino acid positions (numbering corresponding to alignment of the amino acid sequence with SEQ ID No. 1):

at position 156 Gly is substituted by Ser, Thr, Cys, Tyr, Asn, Gln or Trp, preferably Ser, Cys or Tyr; and/or at position 161 Gln is substituted by Ala, Val, Ile, Leu, Phe, Tyr, Trp or Gly, preferably Phe or Gly; and/or at position 180 Glu is substituted by Asp, Asn, Gin, preferably Asp, and/or at position 186 Ala is substituted by Val, Ile, Leu, Met, Phe, Tyr, Trp, Ser, Cys or Thr, preferably Tyr, Cys or Leu; and/or at position 218 Ala is substituted by Val, Ile, Leu, Met, Phe, Tyr, Trp, Cys, Gly or Thr, preferably Ile, Val, Phe or Tyr; and/or at position 222 Asn is substituted by Gin, Asp, Glu, Cys, Thr, Phe, Tyr, Trp, Arg, Lys or His, preferably Cys, Asp, Arg or Phe; and/or at position 235 Lys is substituted by Arg, His, Ser, Thr, Cys, Ala, Val, Ile or Leu, preferably Arg, His, Cys or Val; and/or at position 242 Val is substituted by Arg, His or Lys, preferably His; and/or at position 261 Arg is substituted by His, Lys, Asp, Glu, Ala, Val, Leu or Phe, preferably Asp, Phe, His or Val; and/or at position 315 Leu is substituted by Ser, Thr or Cys, preferably Cys; and/or at position 342 Thr is substituted by Ser or Cys, preferably Cys; and/or at position 349 Gly is substituted by Ser, Thr or Cys, preferably Ser or Cys; and/or at position 350 Gly is substituted by Ser, Thr, Cys, Tyr, Trp or Phe, preferably Ser, Tyr, Phe or Cys; and/or at position 356 Tyr is substituted by Ala, Val, Ile, Leu, Phe or Trp, preferably Val or Phe; and/or at position 438 Pro is substituted by Arg, His or Lys, preferably His.

Also preferably, in the mutated α2,6-transsialidase used in making the HMO mixtures of this invention, the amino acid sequence which is substantially identical, particularly at least 90% identical, with SEQ ID No. 1 has at least two, preferably at least three, mutations at amino acid positions selected from the group consisting of amino acid positions as follows (numbering corresponding to alignment of the amino acid sequence with SEQ ID No. 1):

156 which is substituted by Ser, Thr, Cys, Tyr, Asn, Gln or Trp, preferably Ser, Cys or Tyr;

161 which is substituted by Ala, Val, Ile, Leu, Phe, Tyr, Trp or Gly, preferably Phe or Gly;

180 which is substituted by Asp, Asn, Gin, preferably Asp;

186 which is substituted by Val, Ile, Leu, Met, Phe, Tyr, Trp, Ser, Cys or Thr, preferably Tyr, Cys or Leu;

218 which is substituted by Val, Ile, Leu, Met, Phe, Tyr, Trp, Cys, Gly or Thr, preferably Ile, Val, Phe or Tyr;

222 which is substituted by Gin, Asp, Glu, Cys, Thr, Phe, Tyr, Trp, Arg, Lys or His, preferably Cys, Asp, Arg or Phe;

235 which is substituted by Arg, His, Ser, Cys, Ala, Val, Ile or Leu, preferably Arg, His, Cys or Val;

242 which is substituted by Arg, His or Lys, preferably His;

261 which is substituted by His, Lys, Asp, Glu, Ala, Val, Leu or Phe, preferably Asp, Phe, His or Val;

315 which is substituted by Ser, Thr or Cys, preferably Cys;

342 which is substituted by Ser or Cys, preferably Cys;

349 which is substituted by Ser, Thr or Cys, preferably Ser or Cys;

350 which is substituted by Ser, Thr, Cys, Tyr, Trp or Phe, preferably Ser, Tyr, Phe or Cys;

356 which is substituted by Ala, Val, Ile, Leu, Phe or Trp, preferably Val or Phe; and 438 which is substituted by Arg, His or Lys, preferably His.

These mutated α2,6-transsialidases are characterized by even more improved regioselectivity towards the terminal galactosyl moiety vs an internal galactosyl moiety of LNnT compared to the one-point mutated enzymes disclosed above in transsialidase and/or sialyl transferase reactions.

According to a preferred embodiment, in the mutated α2,6-transsialidase, the amino acid sequence which is substantially identical, particularly at least 90% identical, with SEQ ID No. 1 has at least two, preferably at least three, mutations at amino acid positions selected from the group consisting of amino acid positions as follows (numbering corresponding to alignment of the amino acid sequence with SEQ ID No. 1):

substitution of the amino acid at position 156 by Ser, Thr, Cys, Tyr, Asn, Gln or Trp, preferably Ser, Cys or Tyr;

substitution of the amino acid at position 218 by Val, Ile, Leu, Met, Phe, Tyr, Trp, Cys, Gly or Thr, preferably Ile, Val, Phe or Tyr;

substitution of the amino acid at position 222 by Gln, Asp, Glu, Cys, Thr, Phe, Tyr, Trp, Arg, Lys or His, preferably Cys, Asp, Arg or Phe; and substitution of the amino acid at position 349 by Ser, Thr or Cys, preferably Ser or Cys.

According to a more preferred embodiment, in the mutated α2,6-transsialidase, the amino acid sequence which is substantially identical with the amino acid sequence of SEQ ID No. 1, is preferably the amino acid sequence of the sialyl transferase from *P. leiognathi* JT-SHIZ-119 or its Δ2-15 truncated variant, the sialyl transferase from *P. leiognathi* JT-SHIZ-145 or its Δ2-15 truncated variant, or the sialyl transferase from *P. damselae* JT0160 or its Δ2-15 truncated variant, comprising at least two, preferably at least three, mutations at amino acid positions selected from the group consisting of the following positions as follows (numbering corresponding to alignment of the amino acid sequence with SEQ ID No. 1):

at position 156 Gly is substituted by Ser, Thr, Cys, Tyr, Asn, Gln or Trp, preferably Ser, Cys or Tyr;

at position 218 Ala or Ser is substituted by Val, Ile, Leu, Met, Phe, Tyr, Trp, Cys, Gly or Thr, preferably Ile, Val, Phe or Tyr;

at position 222 Asn or Ser is substituted by Gln, Asp, Glu, Cys, Thr, Phe, Tyr, Trp, Arg, Lys or His, preferably Cys, Asp, Arg or Phe; and at position 349 Gly is substituted by Ser, Thr or Cys, preferably Ser or Cys.

According to a yet more preferred embodiment, in the mutated α2,6-transsialidase, the amino acid sequence which is substantially identical, particularly at least 90% identical, with the amino acid sequence of SEQ ID No. 1 is preferably the sialyl transferase from *P. leiognathi* JT-SHIZ-119 or its Δ2-15 truncated variant, or the sialyl transferase from *P. leiognathi* JT-SHIZ-145 or its Δ2-15 truncated variant, comprising at least two, preferably at least three, mutations at amino acid positions selected from the group consisting of the following positions (numbering corresponding to alignment of the amino acid sequence with SEQ ID No. 1):

at position 156 Gly is substituted by Ser, Thr, Cys, Tyr, Asn, Gln or Trp, preferably Ser, Cys or Tyr;

at position 218 Ala is substituted by Val, Ile, Leu, Met, Phe, Tyr, Trp, Cys, Gly or Thr, preferably Ile, Val, Phe or Tyr;

at position 222 Asn or Ser is substituted by Gln, Asp, Glu, Cys, Thr, Phe, Tyr, Trp, Arg, Lys or His, preferably Cys, Asp, Arg or Phe; and at position 349 Gly is substituted by Ser, Thr or Cys, preferably Ser or Cys.

According to an even more preferred embodiment, in the mutated α2,6-transsialidase, the an amino acid sequence which is substantially identical, particularly at least 90% identical, with the amino acid sequence of SEQ ID No. 1 is preferably the sialyl transferase from *P. leiognathi* JT-SHIZ-119 or its Δ2-15 truncated variant, comprising at least two, preferably at least three, mutations at amino acid positions selected from the group consisting of the following positions as follows:

at position 156 Gly is substituted by Ser, Thr, Cys, Tyr, Asn, Gln or Trp, preferably Ser, Cys or Tyr;

at position 218 Ala is substituted by Val, Ile, Leu, Met, Phe, Tyr, Trp, Cys, Gly or Thr, preferably Ile, Phe or Tyr;

at position 222 Asn is substituted by Gln, Asp, Glu, Cys, Thr, Phe, Tyr, Trp, Arg, Lys or His, preferably Cys, Asp, Arg or Phe; and at position 349 Gly is substituted by Ser, Thr or Cys, preferably Ser or Cys.

According to an especially preferred embodiment, in the mutated α2,6-transsialidase, the amino acid sequence which is substantially identical, particularly at least 90% identical, with the amino acid sequence of SEQ ID No. 1 is the sialyl transferase from *P. leiognathi* JT-SHIZ-119 or its Δ2-15 truncated variant, contains the following mutations: A218Y, N222R and G349S (numbering corresponding to alignment of the amino acid sequence with SEQ ID No. 1).

Besides the regioselectivity, it is important that the transsialidase activity of the α2,6-transsialidase is greater than its hydrolytic activity. In the course of the 6'-SL+LNnT⇌LSTc+Lac reaction the hydrolysis of LST c may become significant at a certain time point, due to the increasing concentration of LST c, which is then degraded into LNnT and sialic acid. In order to prepare the HMO mixtures of the invention, the reaction should be stopped before there is significant product hydrolysis. This time point can be easily determined by well-known enzyme kinetic measurements.

The α2,6-transsialidases for making the HMO mixtures of this invention are preferably selected from the α2,6-transsialidases that lack hydrolytic activity, or at least have significantly reduced hydrolytic activity, and have a high degree of regioselectivity as discussed above.

In carrying out the process of this invention, particular relative concentrations of the 6'-SL donor, LNnT acceptor, the α2,6-transsialidase, the aqueous solvent and the incubation buffer (e.g. 100 mM $KHPO_4$) are not critical. In this regard, the process can be suitably carried out at room temperature (e.g. 15-50, preferably 20-37° C.) at a pH of 6-8, preferably at around 6, for 15 min to 24 hours.

In one preferred embodiment, any of the HMO mixtures of the invention are produced by a microorganism genetically modified to express an α2,6-transsialidase as described above. Methods of genetic modifications of microorganisms for recombinant production of biologically active molecules and molecular manipulation of enzyme molecules are well-known in the art, see e.g. Green MR & Sambrook J: *Molecular Cloning: A Laboratory Manual*, 4th ed, 2012, CSHL PRESS.

Use of the HMO Mixtures of the Invention

Surprisingly, the HMO mixtures containing 6'-SL, LNnT and LST c are anti-infective compositions, therefore they can be advantageously used for treating viral and/or bacterial infections, especially infections of the respiratory tract.

Accordingly, in one embodiment, the anti-infective compositions of this invention can be a pharmaceutical composition. The pharmaceutical composition may further contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition of the invention may also contain other materials that do not produce an adverse, allergic or otherwise unwanted reaction when administered to a patient. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or nonaqueous techniques.

In another embodiment, the anti-infective compositions of this invention can be nutritional compositions. For example, a nutritional composition can be formulated as a rehydration solution or a dietary maintenance or supplement for elderly individuals or immunocompromised individuals. Macronutrients such as edible fats, carbohydrates and proteins can also be included in such nutritional compositions. Edible fats include, for example, coconut oil, soy oil and monoglycerides and diglycerides. Carbohydrates include, for example, glucose, edible lactose and hydrolysed cornstarch. Proteins include, for example, soy protein, whey, and skim milk. Vitamins and minerals (e.g. calcium, phosphorus, potassium, sodium, chloride, magnesium, manganese, iron, copper, zinc, selenium, iodine, and vitamins A, E, D, C, and B complex) can also be included in such nutritional compositions.

The anti-infective compositions of this invention can be administered orally, e.g. as a tablet, capsule, or pellet containing a predetermined amount of the first or the second mixture, or as a powder or granules containing a predetermined concentration of the first mixture or the second mixture, or a gel, paste, solution, suspension, emulsion, syrup, bolus, electuary, or slurry, in an aqueous or nonaqueous liquid, containing a predetermined concentration of the first or the second mixture. Orally administered composition can include binders, lubricants, inert diluents, flavouring agents, and humectants. Orally administered compositions such as tablets can optionally be coated and can be formulated so as to provide sustained, delayed or controlled release of the first or the second mixture therein.

The anti-infective compositions of this invention, advantageously a pharmaceutical composition, can also be administered by rectal suppository, aerosol tube, naso-gastric tube or direct infusion into the GI tract or stomach.

Anti-infective pharmaceutical compositions of this invention can also additionally include therapeutic agents such as antiviral agents, antibiotics, probiotics, analgesics, and anti-inflammatory agents. The proper dosage of these compositions for a patient can be determined in a conventional manner, based upon factors such as the patient's immune status, body weight and age. In some cases, the dosage will be at a concentration similar to that found for 6'-SL, LNnT and/or LST c in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by methods known to those skilled in the art.

In another aspect, the invention provides a method of modulating the microbiome of a human, in particular a non-infant individual, to increase *Bifidobacterium* abundance. The method comprises administering, to said human, 6'-SL, LNnT and LST c, advantageously the first or second mixture of this invention, more advantageously the first mixture, as described above.

"Non-infant human", "non-infant individual" or "non-infant" preferably means a human of 3 years of age and older. A non-infant human can be a child, a teenager, an adult or an elderly person.

In still another aspect, the invention provides a method of preventing or treating viral and/or bacterial infections, especially infections of the respiratory tract, in a human, in particular a non-infant individual. The method comprises administering, to the human, a mixture of 6'-SL, LNnT and LST c, advantageously the first or second mixture of this invention, more advantageously the first mixture, as described above.

Whilst the invention has been described with reference to a preferred embodiment, it will be appreciated that various modifications are possible within the scope of the invention.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

EXAMPLES

Example 1

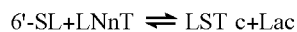

6'-SL+LNnT ⇌ LST c+Lac

Mutants of *Photobacterium leiognathi* JT-SHIZ-119 sialyl transferase truncated by its signal peptide (Δ2-15) were tested, the positions of mutation are according to SEQ ID No. 1.

The test were run in potassium phosphate buffer (100 mM, pH=6.0) at 30° C. in 100-200 μl scale using 50 mM of LNnT and 50 mM of 6'-SL with ⅒ volumes of crude enzyme extract. Samples (20 μl) were taken at time points given below. Reactions were stopped by adding 20 μl of a mixture acetonitrile-ammonium formate (10 mM, pH=4.0) 4:1. Subsequently 160 μl of distilled water were added, samples were mixed again, centrifuged and analyzed with HPLC (5 μl injection). A Kinetix 2.6μ HILIC 100A-column (150×4.6 mm) was used at 40° C. column oven temperature with a flow-rate of 2.5 ml/min using 81% of acetonitrile and 19% of ammonium-formate buffer (10 mM, pH=4.0) as mobile phase. Eluted substrates and products were detected at 200 nm.

For all calculations the peak areas of LNnT and the individual sialylated products (compounds A, B and C, see Scheme 1) were normalized according to their respective numbers of N-acetyl residues as follows:

normalized peak area of LNnT=peak area of LNnT normalized peak area of compound A=½·peak area of compound A normalized peak area of compound B=½·peak area of compound B normalized peak area of compound C=⅓·peak area of compound C.

The concentrations of individual products [mM] were calculated as (assuming that the sum of concentration of LNnT and of all products is 50 mM):

$$\text{product [mM]} = 50 \cdot \frac{\text{product [normalized peak area]}}{\sum \text{products [normalized peak area]} + LNnT\text{[normalized peak area]}}.$$

The total conversion of LNnT to products was calculated as:

$$\text{conversion [\%]} = \frac{100}{50} \cdot \sum \text{products [mM]}.$$

Product purity of compound A (LST c) was calculated as $$100 \cdot \frac{\text{compound } A \text{ [mM]}}{\text{compound } A \text{ [mM]} + \text{compound } B \text{ [mM]} + \text{compound } C \text{ [mM]}}.$$

| mutant | conversion (%) | purity (≥ %) |
|---|---|---|
| A218Y-N222R-G349S | 20 | 100 |
|  | 34 | 100 |
|  | 47 | 99 |
|  | 54 | 97 |
| A218Y-N222R-G349S-S412P-D451K | 16 | 100 |
|  | 24 | 100 |
|  | 47 | 99 |
|  | 49 | 97 |
| A218Y-N222R-G349S-S412P | 20 | 100 |
|  | 31 | 100 |
|  | 48 | 99 |
|  | 50 | 95 |

From the data it could be estimated that the only product formed in the above enzymatic syntheses is compound A (LST c) when the conversion is <45%. Accordingly, the following mixtures could be obtained (lactose is equimolar to LST c):

| conversion | 6'-SL (mol %) | LNnT (mol %) | LST c (mol %) |
|---|---|---|---|
| 16% | 42% | 42% | 8% |
| 20% | 40% | 40% | 10% |
| 24% | 38% | 38% | 12% |
| 31% | 34.5% | 34.5% | 15.5% |
| 34% | 33% | 33% | 17% |
| 45% | 27.5% | 27.5% | 22.5% |

Example 2

A total of 20 male and female patients are recruited to participate in the study. After a screening visit and run-in period of 1-2 weeks, the patients are selected and randomized into two groups, each of 10 patients. One group is administered the treatment product containing 5 grams of a combination of LNnT, 6'-SL and LST c, and one group the placebo product (2 grams of glucose) for 8 weeks. The treatment product and the placebo are in powder form in a unit dosage container.

The patients are eligible to participate if they are at least 18 years of age. All recruited patients are able and willing to understand and comply with the study procedures. Patients are excluded if: they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and pregnant or lactating.

At the screening visit, medical history and concomitant medication is registered and a blood sample for safety analyses is collected. A faecal sample kit is distributed. Patients are instructed to keep their samples in the freezer until the next visit.

At the second visit, eligibility criteria are checked and eligible subjects are randomised to the three arms in the trial. The faecal samples are collected and equipment for new samples are distributed. Patients are familiarised with an interactive internet enabled system which records data daily and are provided with either treatment or control products. Subjects are reminded not to change their usual diet during the study. Blood samples are collected for biomarker studies. The faecal samples are stored at −80° C. until analysis. Faecal samples are subjected to 16S rRNA sequencing analysis.

The study runs for 8 weeks with the patients consuming either a placebo or a treatment product daily. Patients are instructed to consume the products in the morning with breakfast. Compliance is monitored through the interactive internet enabled system. The patients also use the system to record:

Bristol Stool Form Scale (BSFS) information,
symptom information such as abdominal pain, abdominal discomfort, abdominal cramping, abdominal bloating, and abdominal fullness,
additional Gastrointestinal Symptom Rating Scale (GSRS) information.

This questionnaire includes 15 items covering five dimensions (abdominal pain, indigestion, reflux, diarrhea, constipation) and uses a seven-graded Likert scale.

At the end of the study, each patient has an exit visit with the medical team. Faecal samples and blood samples are collected and analysed as before.

The faecal analysis indicates that the treatment patients have increased abundance of *Bifidobacterium*.

Example 3

Ten 5-day old Sprague-Dawley rats are individually housed to avoid contamination between rats and provided with irradiated food and water. The rats are separated into 2 groups of 5 rats: a treatment group and a control group.

A mixture of LNnT, 6'-SL and LST c is added to the drinking water of the treatment group at a total concentration of 40 mg/ml. The water of the control group is not altered (Day 0). Fresh water is administered daily and all rats have free access to the drinking water. The rats are fed a rodent chow and are given fresh chow daily.

Two days after administration of the mixture (Day 2), the rats of both groups are infected by means of oral gavage with an encapsulated *S. pneumoniae* strain.

After 24 hours, the rats are subjected to nasal washing using a saline solution. The solution is recovered and the number of viable bacteria is obtained by counting colonies on agar plates. The rats are monitored for 1 week and are then euthanized (Day 10). The lungs are harvested. Fresh stool pellets are obtained at Day 0, 3 and 10. The samples are immediately frozen and stored at −80° C. DNA is extracted using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 (Klindworth et al. *Nucleic Acids Res.* 41, e1 (2013)) with Illumina adapters attached. These are universal bacterial 16S rDNA primers, which target the V3-V4 region. The following PCR program is used: 98° C. for 30 sec, 25×(98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8×(98° C. for 10 s, 55° C. for 20 s, 72° C. for 20 s), 72° C. for 5 min. Attachment of primers is verified by running the products on a 1% agarose gel.

Products from the nested PCR are normalized using the SequalPrep Normalization Plate Kit and pooled. Pooled libraries are concentrated by evaporation and the DNA concentration of pooled libraries wisas measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, 2013) is used for bioinformatical analysis of the sequence data.

In the HMO (LNnT, 6'-SL and LST c) treated rats, *S. pneumoniae* colonisation of the lungs is reduced compared to the control rats. Similarly, the quantity of viable *S. pneumonia* recovered in the nasal wash of the treated rats is reduced compared to the control rats.

The invention claimed is:

1. A process for obtaining a mixture of human milk oligosaccharides (HMOs) consisting essentially of 6'-O-sialyllactose (6'-SL), lacto-N-neotetraose (LNnT) and sialyllacto-N-tetraose c (LST c), comprising the steps of reacting 6'-SL and LNnT in the presence of an α2,6-transsialidase to produce a reaction medium, and then removing lactose and the α2,6-transsialidase from the reaction medium.

2. A process for obtaining a mixture of human milk oligosaccharides (HMOs) consisting essentially of 6'-O-sialyllactose (6'-SL), lacto-N-neotetraose (LNnT), sialyllacto-N-tetraose c (LST c) and lactose, comprising the steps of reacting 6'-SL and LNnT in the presence of an α2,6-transsialidase to produce a reaction medium, and then removing the α2,6-transsialidase from the reaction medium.

3. The process according to claim 2, comprising the step of reacting 6'-SL and LNnT in a molar ratio of 1:3 to 3:1 in the presence of an α2,6-transsialidase having a conversion rate of at least 20%, up to about 55%, for the reaction of 6'-SL and LNnT.

4. The process according to claim 3, comprising the step of reacting 6'-SL and LNnT in a molar ratio of 1:1, in the presence of an α2,6-transsialidase having a conversion rate of at least 20%, up to about 45%, for the reaction of 6'-SL and LNnT.

5. The process according to claim 3, wherein the conversion rate for the reaction of 6'-SL and LNnT is 30-45%.

6. The process according to claim 1, wherein the α2,6-transsialidase is a mutated α2,6-transsialidase that comprises an amino acid sequence with at least 60% identity to SEQ ID No. 1, and further comprises at least one mutation selected from the group consisting of:

at position 156, an amino acid selected from the group consisting of Ser, Thr, Cys, Tyr, Asn, Gln and Trp, at position 161, an amino acid selected from the group consisting of Ala, Val, Ile, Leu, Phe, Tyr, Trp and Gly at position 180, an amino acid selected from the group consisting of Asp, Asn and Gln;

at position 186, an amino acid selected from the group consisting of Val, Ile, Leu, Met, Phe, Tyr, Trp, Ser, Cys and Thr at position 218, an amino acid selected from the group consisting of Val, Ile, Leu, Met, Phe, Tyr, Trp, Cys, Gly and Thr at position 222, an amino acid selected from the group consisting of Gln, Asp, Glu, Cys, Thr, Phe, Tyr, Trp, Arg, Lys and His;

at position 235, an amino acid selected from the group consisting of Arg, His, Ser, Cys, Ala, Val, Ile or Leu at position 242, an amino acid selected from the group consisting of Arg, His and Lys;

at position 261, an amino acid selected from the group consisting of His, Lys, Asp, Glu, Ala, Val, Leu and Phe;

at position 315, an amino acid selected from the group consisting of Ser, Thr and Cys;

at position 342, an amino acid selected from the group consisting of Ser and Cys;

at position 349, an amino acid selected from the group consisting of Ser, Thr and Cys;

at position 350, an amino acid selected from the group consisting of Ser, Thr, Cys, Tyr, Trp and Phe;

at position 356, an amino acid selected from the group consisting of Ala, Val, Ile, Leu, Phe and Trp; and at position 438, an amino acid selected from Arg, His and Lys.

7. The process according to claim 6, wherein the at least one mutation is selected from the group consisting of:
at position 156 Gly is substituted by Ser, Cys or Tyr;
at position 161 Gln is substituted by Phe or Gly;
at position 180 Glu is substituted by Asp,
at position 186 Ala is substituted by Tyr, Cys or Leu;
at position 218 Ala is substituted by Ile, Val, Phe or Tyr;
at position 222 Asn is substituted by Cys, Asp, Arg or Phe;
at position 235 Lys is substituted by Arg, His, Cys or Val;
at position 242 Val is substituted by His;
at position 261 Arg is substituted by Asp, Phe, His or Val;
at position 315 Leu is substituted by Cys;
at position 342 Thr is substituted by Cys;
at position 349 Gly is substituted by Ser or Cys;
at position 350 Gly is substituted by Ser, Tyr, Phe or Cys;
at position 356 Tyr is substituted by Val or Phe; and
at position 438 Pro is substituted by His.

8. The process according to claim 7, wherein the mutated α2,6-transsialidase has a mutation at least at two amino acid positions from 156, 218, 222 and 349.

9. A method of modulating the microbiome of a human to increase *Bifidobacterium* abundance, the method comprising administering, to the human, a mixture of human milk oligosaccharides (HMOs) consisting essentially of 6'-O-sialyllactose (6'-SL), lacto-N-neotetraose (LNnT) and sialyllacto-N-tetraose c (LST c), and optionally, lactose.

10. A method of preventing or treating viral or bacterial infections in a human, the method comprising administering, to the human, a mixture of human milk oligosaccharides (HMOs) consisting essentially of 6'-O-sialyllactose (6'-SL), lacto-N-neotetraose (LNnT) and sialyllacto-N-tetraose c (LST c), and optionally, lactose.

11. The process according to claim 1, wherein the mixture comprises a molar ratio of LST c relative to the combination of 6'-SL and LNnT of at least 1:18.

12. The process according to claim 1, wherein the mixture comprises a molar ratio of 6'-SL relative to LNnT of 0.18-5.5.

13. The process according to claim 2, wherein the mixture comprises a molar ratio of the combination of 6'-SL and LNnT relative to LST c of 2-18, and the molar ratio of lactose relative to LST c of about 1.

14. The process according to claim 2, wherein the mixture comprises a molar ratio of 6'-SL to LST c of not more than 4 or a molar ratio of LNnT to LST c of not more than 4.

15. The process according to claim 2, wherein the mixture comprises a molar ratio of 6'-SL to LNnT of 0.18-5.5.

16. The process according to claim 1, comprising the step of reacting 6'-SL and LNnT in a molar ratio of 1:3 to 3:1 in the presence of an α2,6-transsialidase having a conversion rate of at least 20%, up to about 55%, for the reaction of 6'-SL and LNnT.

17. The process according to claim 16, comprising the step of reacting 6'-SL and LNnT in a molar ratio of 1:1, in the presence of an α2,6-transsialidase having a conversion rate of at least 30%, up to about 50%, for the reaction of 6'-SL and LNnT.

18. The process according to claim 2, wherein the α2,6-transsialidase is a mutated α2,6-transsialidase that comprises an amino acid sequence with at least 60% identity to SEQ ID No. 1, and further comprises at least one mutation selected from the group consisting of:
at position 156, an amino acid selected from the group consisting of Ser, Thr, Cys, Tyr, Asn, Gln and Trp,
at position 161, an amino acid selected from the group consisting of Ala, Val, Ile, Leu, Phe, Tyr, Trp and Gly
at position 180, an amino acid selected from the group consisting of Asp, Asn and Gln;
at position 186, an amino acid selected from the group consisting of Val, Ile, Leu, Met, Phe, Tyr, Trp, Ser, Cys and Thr
at position 218, an amino acid selected from the group consisting of Val, Ile, Leu, Met, Phe, Tyr, Trp, Cys, Gly and Thr
at position 222, an amino acid selected from the group consisting of Gln, Asp, Glu, Cys, Thr, Phe, Tyr, Trp, Arg, Lys and His;
at position 235, an amino acid selected from the group consisting of Arg, His, Ser, Cys, Ala, Val, Ile or Leu
at position 242, an amino acid selected from the group consisting of Arg, His and Lys;
at position 261, an amino acid selected from the group consisting of His, Lys, Asp, Glu, Ala, Val, Leu and Phe;
at position 315, an amino acid selected from the group consisting of Ser, Thr and Cys;
at position 342, an amino acid selected from the group consisting of Ser and Cys;
at position 349, an amino acid selected from the group consisting of Ser, Thr and Cys;
at position 350, an amino acid selected from the group consisting of Ser, Thr, Cys, Tyr, Trp and Phe;
at position 356, an amino acid selected from the group consisting of Ala, Val, Ile, Leu, Phe and Trp; and
at position 438, an amino acid selected from Arg, His and Lys.

19. The process according to claim 18, wherein the at least one mutation is selected from the group consisting of:
at position 156 Gly is substituted by Ser, Cys or Tyr;
at position 161 Gln is substituted by Phe or Gly;
at position 180 Glu is substituted by Asp,
at position 186 Ala is substituted by Tyr, Cys or Leu;
at position 218 Ala is substituted by Ile, Val, Phe or Tyr;
at position 222 Asn is substituted by Cys, Asp, Arg or Phe;
at position 235 Lys is substituted by Arg, His, Cys or Val;
at position 242 Val is substituted by His;
at position 261 Arg is substituted by Asp, Phe, His or Val;
at position 315 Leu is substituted by Cys;

at position 342 Thr is substituted by Cys;
at position 349 Gly is substituted by Ser or Cys;
at position 350 Gly is substituted by Ser, Tyr, Phe or Cys;
at position 356 Tyr is substituted by Val or Phe; and
at position 438 Pro is substituted by His.

20. The process according to claim 19, wherein the mutated α2,6-transsialidase has a mutation at least at two amino acid positions from 156, 218, 222 and 349.

* * * * *

SEQUENCE LISTING

```
<160> NUMBER OF SEQ ID NOS: 3

<210> SEQ ID NO 1
<211> LENGTH: 497
<212> TYPE: PRT
<213> ORGANISM: Photobacterium leiognathi JT-SHIZ-119

<400> SEQUENCE: 1

Met Cys Asn Asp Asn Gln Asn Thr Val Asp Val Val Ser Thr Val
1               5                   10                  15

Asn Asp Asn Val Ile Glu Asn Asn Thr Tyr Gln Val Lys Pro Ile Asp
                20                  25                  30

Thr Pro Thr Thr Phe Asp Ser Tyr Ser Trp Ile Gln Thr Cys Gly Thr
            35                  40                  45

Pro Ile Leu Lys Asp Asp Glu Lys Tyr Ser Leu Ser Phe Asp Phe Val
    50                  55                  60

Ala Pro Glu Leu Asp Gln Asp Glu Lys Phe Cys Phe Glu Phe Thr Gly
65                  70                  75                  80

Asp Val Asp Gly Lys Arg Tyr Val Thr Gln Thr Asn Leu Thr Val Val
                85                  90                  95

Ala Pro Thr Leu Glu Val Tyr Val Asp His Ala Ser Leu Pro Ser Leu
            100                 105                 110

Gln Gln Leu Met Lys Ile Ile Gln Gln Lys Asn Glu Tyr Ser Gln Asn
        115                 120                 125

Glu Arg Phe Ile Ser Trp Gly Arg Ile Gly Leu Thr Glu Asp Asn Ala
    130                 135                 140

Glu Lys Leu Asn Ala His Ile Tyr Pro Leu Ala Gly Asn Asn Thr Ser
145                 150                 155                 160

Gln Glu Leu Val Asp Ala Val Ile Asp Tyr Ala Asp Ser Lys Asn Arg
                165                 170                 175

Leu Asn Leu Glu Leu Asn Thr Asn Thr Ala His Ser Phe Pro Asn Leu
            180                 185                 190

Ala Pro Ile Leu Arg Ile Ile Ser Ser Lys Ser Asn Ile Leu Ile Ser
```

```
                195                 200                 205
Asn Ile Asn Leu Tyr Asp Asp Gly Ser Ala Glu Tyr Val Asn Leu Tyr
        210                 215                 220
Asn Trp Lys Asp Thr Glu Asp Lys Ser Val Lys Leu Ser Asp Ser Phe
225                 230                 235                 240
Leu Val Leu Lys Asp Tyr Phe Asn Gly Ile Ser Ser Glu Lys Pro Ser
                245                 250                 255
Gly Ile Tyr Gly Arg Tyr Asn Trp His Gln Leu Tyr Asn Thr Ser Tyr
                260                 265                 270
Tyr Phe Leu Arg Lys Asp Tyr Leu Thr Val Glu Pro Gln Leu His Asp
            275                 280                 285
Leu Arg Glu Tyr Leu Gly Gly Ser Leu Lys Gln Met Ser Trp Asp Gly
            290                 295                 300
Phe Ser Gln Leu Ser Lys Gly Asp Lys Glu Leu Phe Leu Asn Ile Val
305                 310                 315                 320
Gly Phe Asp Gln Glu Lys Leu Gln Gln Glu Tyr Gln Gln Ser Glu Leu
                325                 330                 335
Pro Asn Phe Val Phe Thr Gly Thr Thr Thr Trp Ala Gly Gly Glu Thr
                340                 345                 350
Lys Glu Tyr Tyr Ala Gln Gln Val Asn Val Val Asn Asn Ala Ile
            355                 360                 365
Asn Glu Thr Ser Pro Tyr Tyr Leu Gly Arg Glu His Asp Leu Phe Phe
        370                 375                 380
Lys Gly His Pro Arg Gly Gly Ile Ile Asn Asp Ile Ile Leu Gly Ser
385                 390                 395                 400
Phe Asn Asn Met Ile Asp Ile Pro Ala Lys Val Ser Phe Glu Val Leu
                405                 410                 415
Met Met Thr Gly Met Leu Pro Asp Thr Val Gly Gly Ile Ala Ser Ser
                420                 425                 430
Leu Tyr Phe Ser Ile Pro Ala Glu Lys Val Ser Phe Ile Val Phe Thr
            435                 440                 445
Ser Ser Asp Thr Ile Thr Asp Arg Glu Asp Ala Leu Lys Ser Pro Leu
        450                 455                 460
Val Gln Val Met Met Thr Leu Gly Ile Val Lys Glu Lys Asp Val Leu
465                 470                 475                 480
Phe Trp Ser Asp Leu Pro Asp Cys Ser Ser Gly Val Cys Ile Ala Gln
                485                 490                 495
Tyr

<210> SEQ ID NO 2
<211> LENGTH: 483
<212> TYPE: PRT
<213> ORGANISM: Photobacterium leiognathi JT-SHIZ-145

<400> SEQUENCE: 2

Met Cys Asn Asp Asn Gln Asn Thr Val Asp Val Val Ser Thr Val
1               5                   10                  15
Asn Asp Asn Val Ile Glu Asn Asn Thr Tyr Gln Val Lys Pro Ile Asp
                20                  25                  30
Thr Pro Thr Thr Phe Asp Ser Tyr Ser Trp Ile Gln Thr Cys Gly Thr
            35                  40                  45
Pro Ile Leu Lys Asp Asp Glu Lys Tyr Ser Leu Ser Phe Asp Phe Val
        50                  55                  60
Ala Pro Glu Leu Asp Gln Asp Glu Lys Phe Cys Phe Glu Phe Thr Gly
```

```
            65                  70                  75                  80
Asp Val Asp Gly Lys Arg Tyr Val Thr Gln Thr Asn Leu Thr Val Val
                    85                  90                  95
Ala Pro Thr Leu Glu Val Tyr Val Asp His Ala Ser Leu Pro Ser Leu
                    100                 105                 110
Gln Gln Leu Met Lys Ile Ile Gln Lys Asn Glu Tyr Ser Gln Asn
                    115                 120                 125
Glu Arg Phe Ile Ser Trp Gly Arg Ile Arg Leu Thr Glu Asp Asn Ala
                    130                 135                 140
Glu Lys Leu Asn Ala His Ile Tyr Pro Leu Ala Gly Asn Asn Thr Ser
145                 150                 155                 160
Gln Glu Leu Val Asp Ala Val Ile Asp Tyr Ala Asp Ser Lys Asn Arg
                    165                 170                 175
Leu Asn Leu Glu Leu Asn Thr Asn Thr Gly His Ser Phe Arg Asn Ile
                    180                 185                 190
Ala Pro Ile Leu Arg Ala Thr Ser Ser Lys Asn Asn Ile Leu Ile Ser
                    195                 200                 205
Asn Ile Asn Leu Tyr Asp Asp Gly Ser Ala Glu Tyr Val Ser Leu Tyr
                    210                 215                 220
Asn Trp Lys Asp Thr Asp Asn Lys Ser Gln Lys Leu Ser Asp Ser Phe
225                 230                 235                 240
Leu Val Leu Lys Asp Tyr Leu Asn Gly Ile Ser Ser Glu Lys Pro Asn
                    245                 250                 255
Gly Ile Tyr Ser Ile Tyr Asn Trp His Gln Leu Tyr His Ser Ser Tyr
                    260                 265                 270
Tyr Phe Leu Arg Lys Asp Tyr Leu Thr Val Glu Thr Lys Leu His Asp
                    275                 280                 285
Leu Arg Glu Tyr Leu Gly Gly Ser Leu Lys Gln Met Ser Trp Asp Thr
                    290                 295                 300
Phe Ser Gln Leu Ser Lys Gly Asp Lys Glu Leu Phe Leu Asn Ile Val
305                 310                 315                 320
Gly Phe Asp Gln Glu Lys Leu Gln Gln Glu Tyr Gln Gln Ser Glu Leu
                    325                 330                 335
Pro Asn Phe Val Phe Thr Gly Thr Thr Thr Trp Ala Gly Gly Glu Thr
                    340                 345                 350
Lys Glu Tyr Tyr Ala Gln Gln Val Asn Val Val Asn Asn Ala Ile
                    355                 360                 365
Asn Glu Thr Ser Pro Tyr Tyr Leu Gly Arg Glu His Asp Leu Phe Phe
                    370                 375                 380
Lys Gly His Pro Arg Gly Gly Ile Ile Asn Asp Ile Ile Leu Gly Ser
385                 390                 395                 400
Phe Asn Asn Met Ile Asp Ile Pro Ala Lys Val Ser Phe Glu Val Leu
                    405                 410                 415
Met Met Thr Gly Met Leu Pro Asp Thr Val Gly Gly Ile Ala Ser Ser
                    420                 425                 430
Leu Tyr Phe Ser Ile Pro Ala Glu Lys Val Ser Phe Ile Val Phe Thr
                    435                 440                 445
Ser Ser Asp Thr Ile Thr Asp Arg Glu Asp Ala Leu Lys Ser Pro Leu
                    450                 455                 460
Val Gln Val Met Met Thr Leu Gly Ile Val Lys Glu Lys Asp Val Leu
465                 470                 475                 480
Phe Trp Cys
```

```
<210> SEQ ID NO 3
<211> LENGTH: 661
<212> TYPE: PRT
<213> ORGANISM: Photobacterium damselae JT0160

<400> SEQUENCE: 3

Met Cys Asn Ser Asp Asn Thr Ser Leu Lys Glu Thr Val Ser Ser Asn
1               5                   10                  15

Ser Ala Asp Val Val Glu Thr Glu Thr Tyr Gln Leu Thr Pro Ile Asp
            20                  25                  30

Ala Pro Ser Ser Phe Leu Ser His Ser Trp Glu Gln Thr Cys Gly Thr
        35                  40                  45

Pro Ile Leu Asn Glu Ser Asp Lys Gln Ala Ile Ser Phe Asp Phe Val
50                  55                  60

Ala Pro Glu Leu Lys Gln Asp Glu Lys Tyr Cys Phe Thr Phe Lys Gly
65                  70                  75                  80

Ile Thr Gly Asp His Arg Tyr Ile Thr Asn Thr Thr Leu Thr Val Val
                85                  90                  95

Ala Pro Thr Leu Glu Val Tyr Ile Asp His Ala Ser Leu Pro Ser Leu
            100                 105                 110

Gln Gln Leu Ile His Ile Ile Gln Ala Lys Asp Glu Tyr Pro Ser Asn
        115                 120                 125

Gln Arg Phe Val Ser Trp Lys Arg Val Thr Val Asp Ala Asp Asn Ala
130                 135                 140

Asn Lys Leu Asn Ile His Thr Tyr Pro Leu Lys Gly Asn Asn Thr Ser
145                 150                 155                 160

Pro Glu Met Val Ala Ala Ile Asp Glu Tyr Ala Gln Ser Lys Asn Arg
                165                 170                 175

Leu Asn Ile Glu Phe Tyr Thr Asn Thr Ala His Val Phe Asn Asn Leu
            180                 185                 190

Pro Pro Ile Ile Gln Pro Leu Tyr Asn Asn Glu Lys Val Lys Ile Ser
        195                 200                 205

His Ile Ser Leu Tyr Asp Asp Gly Ser Ser Gly Tyr Val Ser Leu Tyr
210                 215                 220

Gln Trp Lys Asp Thr Pro Asn Lys Ile Glu Thr Leu Glu Gly Glu Val
225                 230                 235                 240

Ser Leu Leu Ala Asn Tyr Leu Ala Gly Thr Ser Pro Asp Ala Pro Lys
                245                 250                 255

Gly Met Gly Asn Arg Tyr Asn Trp His Lys Leu Tyr Asp Thr Asp Tyr
            260                 265                 270

Tyr Phe Leu Arg Glu Asp Tyr Leu Asp Val Glu Ala Asn Leu His Asp
        275                 280                 285

Leu Arg Asp Tyr Leu Gly Ser Ser Ala Lys Gln Met Pro Trp Asp Glu
290                 295                 300

Phe Ala Lys Leu Ser Asp Ser Gln Gln Thr Leu Phe Leu Asp Ile Val
305                 310                 315                 320

Gly Phe Asp Lys Glu Gln Leu Gln Gln Gln Tyr Ser Gln Ser Pro Leu
                325                 330                 335

Pro Asn Phe Ile Phe Thr Gly Thr Thr Thr Trp Ala Gly Gly Glu Thr
            340                 345                 350

Lys Glu Tyr Tyr Ala Gln Gln Gln Val Asn Val Ile Asn Asn Ala Ile
        355                 360                 365

Asn Glu Thr Ser Pro Tyr Tyr Leu Gly Lys Asp Tyr Asp Leu Phe Phe
370                 375                 380
```

```
Lys Gly His Pro Ala Gly Gly Val Ile Asn Asp Ile Ile Leu Gly Ser
385                 390                 395                 400

Phe Pro Asp Met Ile Asn Ile Pro Ala Lys Ile Ser Phe Glu Val Leu
                405                 410                 415

Met Met Thr Asp Met Leu Pro Asp Thr Val Ala Gly Ile Ala Ser Ser
            420                 425                 430

Leu Tyr Phe Thr Ile Pro Ala Asp Lys Val Asn Phe Ile Val Phe Thr
        435                 440                 445

Ser Ser Asp Thr Ile Thr Asp Arg Glu Glu Ala Leu Lys Ser Pro Leu
    450                 455                 460

Val Gln Val Met Leu Thr Leu Gly Ile Val Lys Glu Lys Asp Val Leu
465                 470                 475                 480

Phe Trp Ala Asp His Lys Val Asn Ser Met Glu Val Ala Ile Asp Glu
                485                 490                 495

Ala Cys Thr Arg Ile Ile Ala Lys Arg Gln Pro Thr Ala Ser Asp Leu
            500                 505                 510

Arg Leu Val Ile Ala Ile Ile Lys Thr Ile Thr Asp Leu Glu Arg Ile
        515                 520                 525

Gly Asp Val Ala Glu Ser Ile Ala Lys Val Ala Leu Glu Ser Phe Ser
530                 535                 540

Asn Lys Gln Tyr Asn Leu Leu Val Ser Leu Glu Ser Leu Gly Gln His
545                 550                 555                 560

Thr Val Arg Met Leu His Glu Val Leu Asp Ala Phe Ala Arg Met Asp
            565                 570                 575

Val Lys Ala Ala Ile Glu Val Tyr Gln Glu Asp Asp Arg Ile Asp Gln
        580                 585                 590

Glu Tyr Glu Ser Ile Val Arg Gln Leu Met Ala His Met Met Glu Asp
        595                 600                 605

Pro Ser Ser Ile Pro Asn Val Met Lys Val Met Trp Ala Ala Arg Ser
        610                 615                 620

Ile Glu Arg Val Gly Asp Arg Cys Gln Asn Ile Cys Glu Tyr Ile Ile
625                 630                 635                 640

Tyr Phe Val Lys Gly Lys Asp Val Arg His Thr Lys Pro Asp Asp Phe
                645                 650                 655

Gly Thr Met Leu Asp
            660
```